United States Patent [19]

Wei et al.

[11] Patent Number: 5,189,157
[45] Date of Patent: Feb. 23, 1993

[54] ANTIBACTERIAL CEPHALOSPORIN COMPOUNDS

[75] Inventors: Ching-Chen Wei, Cedar Knolls; Kevin F. West, Fairfield, both of N.J.

[73] Assignee: Hoffmann La Roche Inc., Nutley, N.J.

[21] Appl. No.: 189,936

[22] Filed: May 3, 1988

Related U.S. Application Data

[63] Continuation-in-part of Ser. No. 62,928, Jun. 16, 1987, abandoned.

[51] Int. Cl.$^5$ ................ C07D 501/34; A61K 31/545
[52] U.S. Cl. ..................................... 540/222; 540/221
[58] Field of Search ................ 514/202; 540/227, 221, 540/222

[56] References Cited

U.S. PATENT DOCUMENTS

| | | | |
|---|---|---|---|
| 3,445,463 | 5/1969 | Van Heymingen | 260/243 |
| 3,823,139 | 7/1974 | Underwood | 260/243 C |
| 3,823,140 | 7/1974 | Clark et al. | 260/243 C |
| 3,880,845 | 4/1975 | Treuner | 260/243 C |
| 4,024,133 | 5/1977 | Cook et al. | 260/243 C |
| 4,033,950 | 7/1977 | Cook et al. | 260/243 C |
| 4,138,555 | 2/1979 | Cook et al. | 544/22 |
| 4,150,223 | 4/1979 | Christensen et al. | 544/16 |
| 4,202,893 | 5/1980 | Heymes et al. | 424/246 |
| 4,279,818 | 7/1981 | Takaya et al. | 424/244 |
| 4,298,606 | 11/1981 | Ochiai et al. | 424/246 |
| 4,393,059 | 7/1983 | Takaya et al. | 424/246 |
| 4,434,287 | 2/1984 | Woodward et al. | 544/16 |
| 4,464,367 | 4/1984 | Labeeuw et al. | 424/246 |
| 4,547,371 | 10/1985 | Doherty et al. | 514/200 |
| 4,550,162 | 10/1985 | Woodward et al. | 544/16 |
| 4,656,166 | 4/1987 | Salhi et al. | 540/226 |
| 4,950,661 | 8/1990 | Olliero et al. | 514/202 |

FOREIGN PATENT DOCUMENTS

| | | |
|---|---|---|
| 80926/87 | 5/1988 | Australia . |
| 0267733 | 5/1888 | European Pat. Off. . |
| 178980 | 4/1986 | European Pat. Off. . |
| 0265185 | 4/1988 | European Pat. Off. . |
| 0269512 | 6/1988 | European Pat. Off. . |
| 2261270 | 9/1975 | France . |
| 2479229 | 3/1980 | France . |
| 1399086 | 6/1975 | United Kingdom . |
| 1576625 | 10/1980 | United Kingdom . |
| 1581854 | 12/1980 | United Kingdom . |
| 1597359 | 9/1981 | United Kingdom . |

*Primary Examiner*—Nicholas S. Rizzo
*Attorney, Agent, or Firm*—George M. Gould; George W. Johnston; Alan P. Kass

[57] ABSTRACT

There are presented antibacterial cephalosporins having broad antimicrobial activity as well as intermediates for their formation, such compounds having the formula

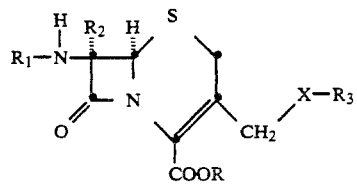

wherein X is

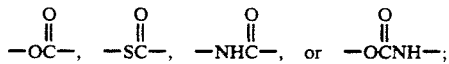

R is hydrogen or a carboxylic acid protecting group;
$R_1$ is hydrogen or an acyl group;
$R_2$ is hydrogen or lower alkoxy; and
$R_3$ is carbocyclic aryl or alkyl carbocyclic aryl substituted on the ring with two or more of hydroxy and/or lower alkanoyl ester groups, with halogen being an optional additional ring substituent;

as well as the corresponding readily hydrolyzable esters, pharmaceutically acceptable salts and hydrates of these compounds where R is hydrogen.

45 Claims, No Drawings

ANTIBACTERIAL CEPHALOSPORIN COMPOUNDS

CROSS-REFERENCE TO RELATED APPLICATION

This is a continuation-in-part of application Ser. No. 07/062,928, filed Jun. 16, 1987, now abandoned.

DESCRIPTION OF THE INVENTION

The present invention relates to intermediates and antibacterial compounds of the formula

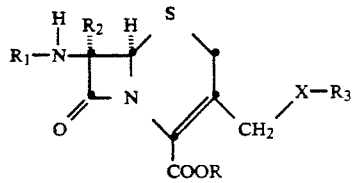

I wherein X is

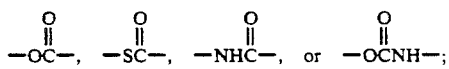

R is hydrogen or a carboxylic acid protecting group;
$R_1$ is hydrogen or an acyl group;
$R_2$ is hydrogen or lower alkoxy; and
$R_3$ is carbocyclic aryl or alkyl carbocyclic aryl, substituted on the ring with two or more members of the group consisting of hydroxy and lower alkyl ester, with halogen being an optional additional ring substituent;

as well as the corresponding readily hydrolyzable esters, pharmaceutically acceptable salts and hydrates of these compounds where R is hydrogen.

As used herein, the terms "lower alkyl" and "alkyl" refer to both straight and branched chain saturated hydrocarbon groups having 1 to 8, and preferably 1 to 4, carbon atoms, for example, methyl, ethyl, propyl, isopropyl, tertiary butyl, and the like.

As used herein, the term "lower alkoxy" refers to a straight or branched chain hydrocarbonoxy group wherein the "alkyl" portion is a lower alkyl group as defined above. Examples include methoxy, ethoxy, propoxy and the like.

The term "halogen", or "halo", used herein refers to all four forms, that is, chloro, bromo, iodo and fluoro, unless specified otherwise.

The term "acyl" used in conjunction with $R_1$ herein refers to all organic radicals derived from an organic acid, such as a carboxylic acid, by removal of the hydroxyl group. Although the group $R_1$ may be any one of many acyl radicals, certain acyl groups are preferred, as described below.

Exemplary acyl groups are those groups which have been used in the past to acylate b-lactam antibiotics, including 6-aminopenicillanic acid and derivatives and 7-aminocephalosporanic acid and derivatives; see, for example, *Cephalosporins and Penicillins*, edited by Flynn, Academic Press (1972), Belgian patent 866,038, published Oct. 17, 1978, Belgian patent 867,994, published Dec. 11, 1978, U.S. Pat. No. 4,152,432, issued May 1, 1979, U.S. Pat. No. 3,971,778, issued Jul. 27, 1976, and U.S. Pat. No. 4,173,199, issued Oct. 23, 1979. The portions of these references describing various acyl groups are incorporated herein by reference. The following list of acyl groups is presented to further exemplify the term "acyl", without intending to limit that term to only those groups set forth:

(a) Aliphatic groups having the formula

wherein $R_5$ is alkyl, cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

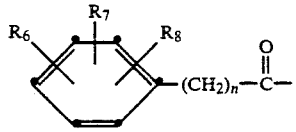

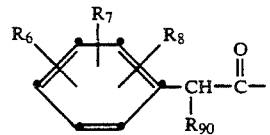

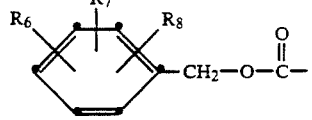

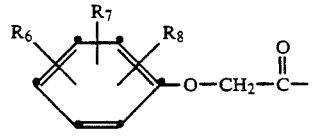

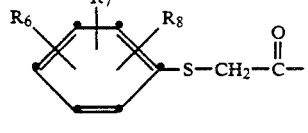

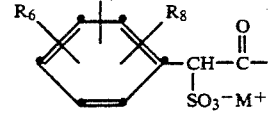

and

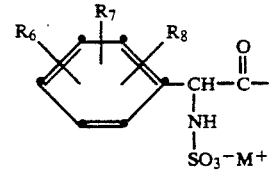

wherein n is 0, 1, 2 or 3; $R_6$, $R_7$, and $R_8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_{90}$ is amino, acylamino, hydroxyl, a carboxyl salt, protected carboxy such as benzyloxycarbonyl, formyloxy or azido.

Preferred carbocyclic aromatic acyl groups include those having the formula

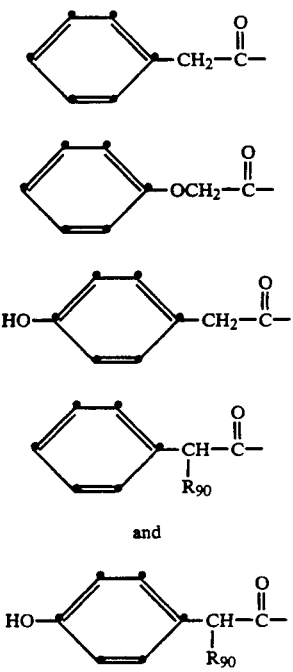

($R_{90}$ is preferably an amino group, a hydroxy group, or a carboxyl salt or sulfo salt).

Examples of other acyl groups suitable for the purposes of the present invention are sulfophenylacetyl, hydroxysulfonyloxyphenylacetyl, sulfamoylphenylacetyl, (phenoxycarbonyl)phenylacetyl, (p-tolyloxycarbonyl)phenylacetyl, formyloxyphenylacetyl, carboxphenylacetyl, formylaminophenylacetyl, benzyloxycarbonylphenylacetyl, 2-(N,N-dimethylsulfamoyl)-2-phenylacetyl, 2-bromo-2-thienylacetyl, etc.

(c) Heteroaromatic groups having the formula

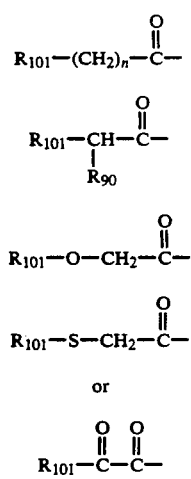

wherein n is 0, 1, 2 or 3; $R_{90}$ is as defined above; and $R_{101}$ is a substituted or unsubstituted 5-, 6- or 7-membered heterocyclic ring containing 1, 2, 3 or 4 (preferably 1 or 2) nitrogen, oxygen or sulfur atoms. Exemplary heterocyclic rings are thienyl, furyl, pyrrolyl, pyridinyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms, or alkoxy of 1 to 4 carbon atoms.

Preferred heteroaromatic acyl groups include those groups of the above formulas wherein $R_{101}$ is 2-amino-4-thiazolyl, 2-amino-5-halo-4-thiazolyl, 4-aminopyridin-2-yl, 2-amino-1,3,4-thiadiazol-5-yl, 2-thienyl, 2-furanyl, 4-pyridinyl or 2,6-dichloro-4-pyridinyl.

(d) [[(4-Substituted-2,3-dioxo-1-piperazinyl)carbonyl]amino]substituted acetyl groups having the formula

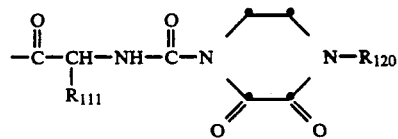

wherein $R_{111}$ is alkyl, hydroxyalkyl or an aromatic group (including carbocylic aromatics) such as those of the formula

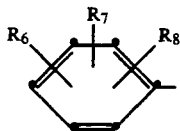

wherein $R_6$, $R_7$ and $R_8$ are as previously defined and heteroaromatics as included within the definition of $R_{101}$; and $R_{120}$ is alkyl, substituted alkyl (wherein the alkyl group is substituted with one or more halogen, cyano, nitro, amino or mercapto groups), e.g., 4-lower alkyl (preferably ethyl or methyl)-2,3-dioxo-1-piperazinecarbonyl-D-phenylglycyl.

(e) (Substituted oxyimino) arylacetyl groups having the formula

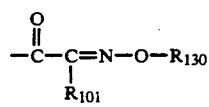

wherein $R_{101}$ is as defined above and $R_{130}$ is hydrogen, lower alkyl and $C_3$–$C_7$ cycloalkyl or substituted lower alkyl (wherein the alkyl group is substituted with 1 or more halogen, cyano, nitro, amino, mercapto, lower alkylthio, aromatic group (as defined by $R_{111}$), carboxyl (including salts thereof), amido, carbamoyl, lower alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, di-lower alkoxyphosphinyl substituents, carboxyl lower alkyl or carboxyl-$C_3$-$C_7$-cycloalkyl.

Examples of the

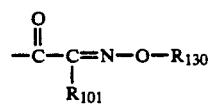

grouping are 2-[(2-chloroacetamidothiazol-4-yl)-2-[p-nitrobenzyloxycarbonyl]methoxyimino]acetyl, 2-(2-chloroacetamidothiazol-4-yl)-2-methoxyiminoacetyl, 2-(2-aminothiazol-4-yl)-2-isopropoxyiminoacetyl, 2-(2-aminothiazol-4-yl)-2-methoxyiminoacetyl, 2-(2-aminothiazol-4-yl)-2-hydroxyiminoacetyl, 2-thienyl-2-methoxyiminoacetyl, 2-furyl-2-methoxyiminoacetyl, 2-(4-hydroxyphenyl)-2-methoxyiminoacetyl, 2-phenyl-2-methoxyiminoacetyl, 2-phenyl-2-hydroxyiminoacetyl, 2-thienyl-2-hydroxyiminoacetyl, 2-thienyl-2-(dichloroacetyloxyimino)acetyl, 2-[4-($\gamma$-D-glutamyloxy)phenyl]-2-hydroxyiminoacetyl, 2-[4-(3-amino-3-carboxypropoxy)phenyl]-2-hydroxyiminoacetyl, 2-(5-chloro-2-chloroacetamidothiazol-4-yl)-2-methoxyiminoacetyl, 2-(5-chloro-2-aminothiazol-4-yl)-2-methoxyiminoacetyl, 2-[2-(t-butoxycarbonyl)isopropoxyimino]-2-(2-sulfoaminothiazol-4-yl)acetyl, 2-[2-(t-butoxycarbonyl)isopropoxyimino]-2-(2-triphenylmethylaminothiazol-4-yl)acetyl, 2-(2-chloroacetamidothiazol-4-yl)-2-isopropoxyiminoacetyl, 2-methoxyimino-2-(2-sulfoaminothiazol-4-yl)acetyl, 2[(2-aminothiazol-4-yl)-2-carboxymethoxyimino]-acetyl, 2[2-(2-mesylaminothiazol-4-yl)-2-isopropoxyiminoacetyl, 2(2-imino-3-mesyl-4-thiazolin-4-yl)-2-isopropoxyiminoacetyl, 2-[(2-aminothiazol-4-yl)-2-(carboxyisopropoxyimino)acetyl, etc.

(f) (Acylamino) substituted acetyl groups having the formula

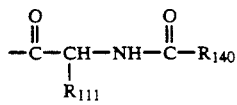

wherein $R_{111}$ is as defined above and $R_{140}$ is

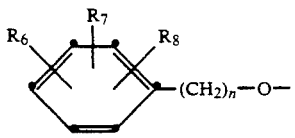

(where $R_6$, $R_7$, $R_8$ and n are as previously defined), hydrogen, lower alkyl, substituted lower alkyl, amino, alkylamino, dialkylamino, (cyanoalkyl)amino, hydrazino, alkyl hydrazino, aryl hydrazino and acyl hydrazino.

Preferred (acylamino)arylacetyl groups of the above formula include those groups wherein $R_{140}$ is amino, or acylamino. Also preferred are those groups wherein $R_{111}$ is phenyl or 2-thienyl.

(g) (Substituted acyloxyimino) substituted acetyl groups having the formula

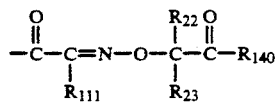

wherein $R_{111}$ and $R_{140}$ are as defined above, and $R_{22}$ and $R_{23}$ are independently selected from the group consisting of hydrogen and lower alkyl, or $R_{22}$ and $R_{23}$ taken together with the carbon atom to which they are attached form a $C_3-C_7$ carbocyclic ring, for example, cyclopropyl, cyclobutyl or cyclopentyl.

Preferred (substituted acylimino) arylacetyl groups of the above formula include those groups wherein $R_{140}$ is amino. Also preferred are those groups wherein $R_{111}$ is 4-thiazolyl.

(h) [[[3-Substituted-2-oxo-1-imidazolidinyl]carbonyl]amino]substituted acetyl groups having the formula

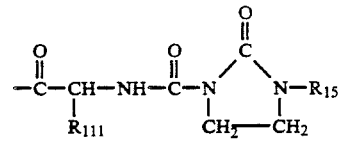

wherein $R_{111}$ is as defined above and $R_{15}$ is hydrogen, alkylsulfonyl, arylmethyleneamino (i.e., —N=CHR$_{111}$ wherein $R_{111}$ is as defined above),

(wherein $R_{16}$ is hydrogen, alkyl or halogen substituted alkyl), aromatic group (as defined by $R_{111}$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino]arylacetyl groups of the above formula include those wherein $R_{111}$ is phenyl or 2-thienyl. Also preferred are those groups wherein $R_{15}$ is hydrogen, methylsulfonyl, phenylmethyleneamino or 2-furylmethyleneamino.

By the term "aryl" is meant a substituted or unsubstituted aromatic moiety, such as, phenyl, tolyl, xylyl, mesityl, cumenyl, naphthyl, and the like, wherein said aryl group may have 1 to 3 suitable substituents, such as, halo (fluoro, chloro, bromo, etc.), hydroxy and the like.

By the term or "lower alkanoyl" or "alkanoyl" as utilized herein is intended a moiety of the formula

wherein $R_{25}$ is H or $C_1$ to $C_6$ lower alkanoic acid, e.g., acetyl, formyl, propionyl, butyryl and the like.

By the term "substituted phenyl" is meant phenyl mono- or di-substituted by halo(chloro, bromo, fluoro, etc.), lower alkyl, amino, nitro or trifluoromethyl.

By the term "substituted alkyl" is meant a "lower alkyl" moiety substituted by, for example, halo(chloro, fluoro, bromo, etc.), trifluoromethyl, amino, cyano, etc.

By the term "lower alkenyl" is meant straight or branched chain hydrocarbon groups which contain an olefinic double bond having 2 to 6 carbon atoms, i.e. the radical of compounds of the formula $C_nH_{2n}$ wherein n is 2 to 6, e.g. alkyl, vinyl, etc.

By the term "aralkyl" is meant a hydrocarbon group having both aromatic and aliphatic structures, that is, a hydrocarbon group in which a lower alkyl hydrogen atom is substituted by a monocyclic aryl group, e.g., phenyl, tolyl, etc.

The expression 5- or 6- membered heterocyclic ring containing 1–3 hetero atoms selected from the group consisting of O, N and S is intended to represent the following groups: pyridyl, piperidyl, piperidino, N-oxido-pyridyl, pyrimidyl, piperazinyl, pyrolidinyl, pyridazinyl, N-oxide-pyridazinyl, etc. a 5-membered nitrogen-containing hetero ring, e.g. pyrazolyl, imidazolyl thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, etc., and others. Each of these hetero rings may be further substituted and, as the substituents, there may be mentioned, for example, lower alkyls such as methyl, ethyl, propyl, etc., lower alkoxys such as methoxy, ethoxy, etc., halogens such as chlorine, bromine, etc., halogen substituted alkyls such as trifluoromethyl, trichloroethyl, etc., amino, mercapto, hydroxyl, carbamoyl, or carboxyl group, etc.

By the term "cycloloweralkyl" is meant a 3-6 membered saturated carbocyclic moiety, e.g. cyclopropyl, cyclobutyl, cyclohexyl, etc.

As readily hydrolyzable esters of the compounds of formula I there are to be understood compounds of formula I, the carboxy group(s) of which (i.e., the 2-carboxy group) is/are present in the form of readily hydrolyzable ester groups. Examples of such esters, which can be of the conventional type, are the lower alkanoyloxyalkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamindomethyl ester). Other esters (e.g., the benzyl and cyanomethyl esters) can also be used.

Examples of salts of the compounds of formula I are alkali metal salts such as the sodium and potassium salt, the ammonium salt, alkaline earth metal salts such as the calcium salt, salts with organic bases such as salts with amines (e.g., salts with N-ethyl-piperidine, procaine, dibenzylamine, N,N'-dibenzylethylenediamine, alkylamines or dialkylamines) as well as salts with amino acids such as, for example, salts with arginine or lysine.

The compounds of formula I as well as their salts and readily hydrolyzable esters can be hydrates. The hydration can be effected in the course of the manufacturing process or can occur gradually as a result of hygroscopic properties of an initially anhydrous product.

A preferred class of compounds are of the formula

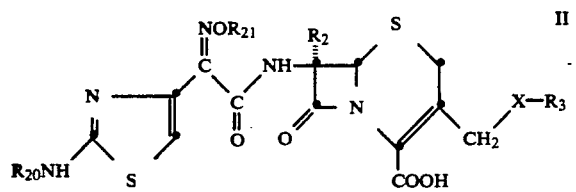

II wherein X, $R_2$ and $R_3$ are as above, $R_{20}$ is hydrogen or an amino protecting group, for example, trityl or chloroacetyl, and $R_{21}$ is hydrogen, lower alkyl or a group of the formula

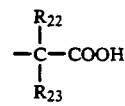

wherein $R_{22}$ and $R_{23}$ are as defined above.

Still more preferred are compounds of the formula II in which $R_{20}$ is hydrogen, and $R_{21}$ is methyl or a group of the formula

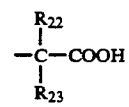

wherein $R_{22}$ and $R_{23}$ are selected from the group consisting of hydrogen and methyl.

Preferably, the

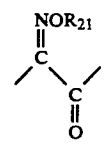

grouping is in the syn-form, i.e., the Z-form.

Another preferred class of compounds are of the formula

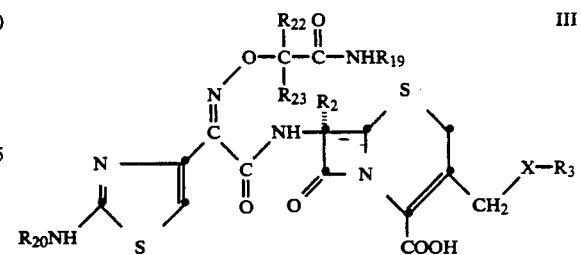

III wherein X, $R_2$ and $R_3$ are as above, $R_{19}$ is hydrogen, lower alkyl, amino, alkyl amino, aryl amino or acyl amino, and $R_{20}$, $R_{22}$ and $R_{23}$ are as defined above.

Still another preferred class of compounds are those of the formula

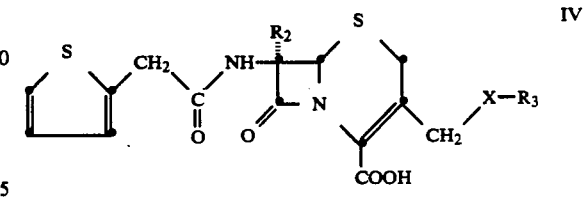

IV wherein X, $R_2$ and $R_3$ are as above.

Also preferred are compounds of the formula

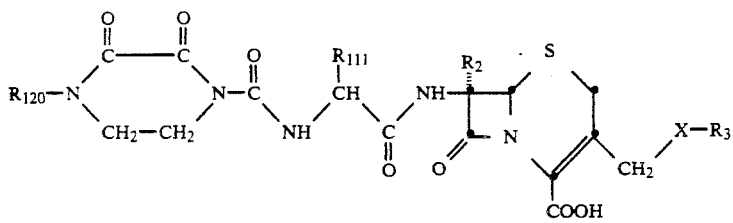

wherein X, $R_2$, $R_3$, $R_{111}$ and $R_{120}$ are defined as above. $R_3$ is preferably of the formula

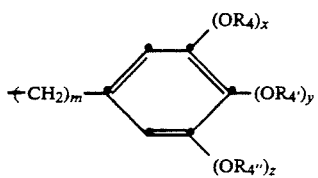

or of the formula

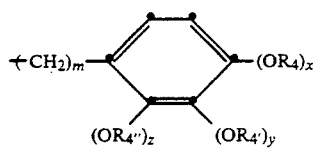

or of the formula

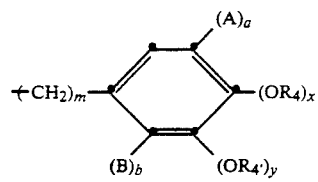

wherein $R_4$, $R_4'$ $R_4''$ are independently hydrogen or

wherein $R_{200}$ is straight or branched loweralkyl, A and B are halogen, a, b, x, y and z are independently zero or 1 except that at least two of x, y and z are always 1, and m is zero or an integer from 1 to 8. When a, b, x, y or z is zero, it should be understood that a hydrogen atom will then be present at that ring position.

Compounds of the Formula I, their salts and esters and hydrates of those compounds can be used as agents to combat bacterial infections (including urinary tract infections and respiratory infections) in mammalian species, e.g., dogs, cats, horses, etc., and humans. These compounds exhibit activity against a broad range of both Gram-negative and Gram-positive bacteria.

The in vitro activity of the compounds of the present invention as measured by the Minimum Inhibitory Concentration in micrograms/ml utilizing the Agar Well Diffusion Method, Agar Dilution Method or Broth Dilution Method against a variety of Gram-positive and Gram-negative organisms, is as follows:

| Compound A: | [6R-[6 alpha,7 beta(Z)]]-7-[[(2-amino-4-thiazolyl)(methoxyimino)acetyl]amino]-3-[[[(3,4-dihydroxyphenyl)carbonyl]oxy]methyl]-8-oxo-5-thia-1-azabicyclo[4.2.0]oct-2-ene-2-carboxylic acid monosodium salt |
| Compound B: | [6R-[6 alpha,7 beta(Z)]]-3-[[[3,4-bis(acetyloxy)benzoyl]oxy]methyl]-7-[[[2-amino-4-thiazolyl][(2-amino-2-oxoethoxy)imino]acetyl]amino]-8-oxo-5-thia-1-azabicyclo[4.2.0]oct-2-ene-2-carboxylic acid monosodium salt |
| Compound C: | [6R-[6 alpha,7 beta(Z)]]-7-[[(2-amino-4-thiazolyl)(1-carboxy-1-methylethoxy)-imino]acetyl]amino]-3-[[(3,4-dihydroxybenzoyl)oxy]methyl]-8-oxo-5-thia-1-azabicyclo[4.2.0]oct-2-ene-2-carboxylic acid disodium salt |
| Compound D: | [6R-[6 alpha,7 beta(R*)]]-7-[[[[(4-ethyl-2,4-dioxo-1-piperazinyl)carbonyl]amino]phenyl acetyl]amino]-3-[[(3,4-dihydroxy)benzoyl]oxy]-methyl]-8-oxo-5-thia-1-azabicyclo(4.2.0)oct-2-ene-2-carboxylic acid monosodium salt |

TABLE 1

In Vitro MIC (mg/ml) Agar Well Diffusion Method

| Culture | Compound A |
|---|---|
| P. aeruginosa 56 | 0.98 |
| P. vulgaris 101N | 0.06 |
| E. coli 1269B | 0.12 |
| K. pneumonia 369 | 0.49 |
| S. marcescens SM | 0.98 |
| S. aureus 1059B | 7.8 |

TABLE 2

In Vitro MIC (µg/ml) Agar Dilution Method

| Culture | Compound B |
|---|---|
| E. coli 48 | 0.031 |
| K. pneumoniae A | 0.125 |
| E. cloacae 9570A | 1 |
| E. cloaca P99 | 32 |
| P. vulgaris ATCC 6380 | 0.016 |
| P. mirabilis 190 | 0.063 |
| S. marscescens SM | 1 |
| P. aeruginosa 130 | 4 |
| P. aeruginosa 185/H | 2 |
| P. aeruginosa Stone 130 | 4 |
| P. aureus Giorgid | 8 |
| S. aureus Smith | 4 |
| S. aureus 95 | 64 |
| S. aureus 1059B | 4 |
| S. aureus ATCC 25923 | 2 |

TABLE 3

In Vitro MIC (µg/ml) Broth Dilution Method

| | Compounds | | |
|---|---|---|---|
| Culture | A | C | D |
| P. aeruginosa B | 2 | 0.125 | 0.25 |
| P. aeruginosa Stone 130 | 2 | 0.125 | 0.5 |
| P. aeruginosa ATCC 27853 | 8 | 32 | 0.5 |
| P. aeruginosa 8710 | 2 | 0.063 | 0.125 |
| P. aeruginosa 503-56 | 4 | 0.25 | 4 |
| P. aeruginosa 8780 | 0.5 | >0.008 | 0.016 |
| P. aeruginosa 6148B | 2 | 0.031 | 0.125 |

TABLE 3-continued

| In Vitro MIC (μg/ml) Broth Dilution Method | | | |
|---|---|---|---|
| | Compounds | | |
| Culture | A | C | D |
| P. aeruginosa 765 | 4 | 8 | 128 |
| P. aeruginosa 185/H | 0.016 | 0.031 | 0.125 |
| P. aeruginosa 1973E | 4 | 2 | 4 |
| P. aeruginosa 5700 | 8 | 2 | 4 |
| P. aeruginosa K77/WT | 1 | 0.63 | 0.25 |
| P. aeruginosa K77/61 | 0.25 | >0.008 | 0.016 |

For combatting bacterial infections in mammals, a compound of this invention (more precisely, a compound of formula I where R is hydrogen and $R_1$ is not hydrogen, or a corresponding hydrolyzable ester or pharmaceutically acceptable salt or hydrate) can be administered to a mammal in an amount of about 5 mg/kg/day to about 500 mg/kg/day, preferably about 10 mg/kg/day to 100 mg/kg/day, most preferably about 10 mg/kg/day to about 55 mg/kg/day.

All modes of administration which have been used in the past to deliver penicillins and cephalosporins to the site of the infection are also contemplated for use with the compounds of the present invention. By way of illustration, such methods of administration include oral, e.g., tablets or capsules parenteral, e.g., intravenous or intramuscular, and enteral, e.g., as a suppository.

The following reaction schemes set forth the methods and intermediates useful in producing the end products of formula I.

In the following reaction sequences, where a substituent group is present which may be attached during the reaction it should be in protected form, utilizing well known protecting groups. For example, amino groups may be protected with easily removable protective groups employed in peptide chemistry, such as an alkoxycarbonyl group, e.g., t-butoxycarbonyl, and the like, a substituted alkoxycarbonyl group, e.g., trichloroethoxycarbonyl, and the like, a substituted alkylcarbonyl, e.g., monochloromethylcarbonyl, or a substituted aralkyloxycarbonyl group, e.g., p-nitrobenzyloxycarbonyl and triphenylmethyl.

A preferred protecting group is tert.-butyloxycarbonyl (t-BOC) or triphenylmethyl.

An ester protecting groups one may utilize an ester form which can be easily converted into a free carboxyl group under mild conditions, the ester protecting group being exemplified by, for example, t-butyl, p-nitrobenzyl, benzhydryl, allyl, etc.

In the following reaction schemes, compounds X in Scheme I, XIII in Scheme III, XVI in Scheme IV and XVII in Scheme V, $R_3$ (as defined above) may be hydroxyaryl or alkanoyl ester thereof. In the case of the alkanoyl esters, conversion to the corresponding hydroxyaryl can be accomplished with the use of an alcohol and a base, preferably methanol and sodium bicarbonate.

Scheme I

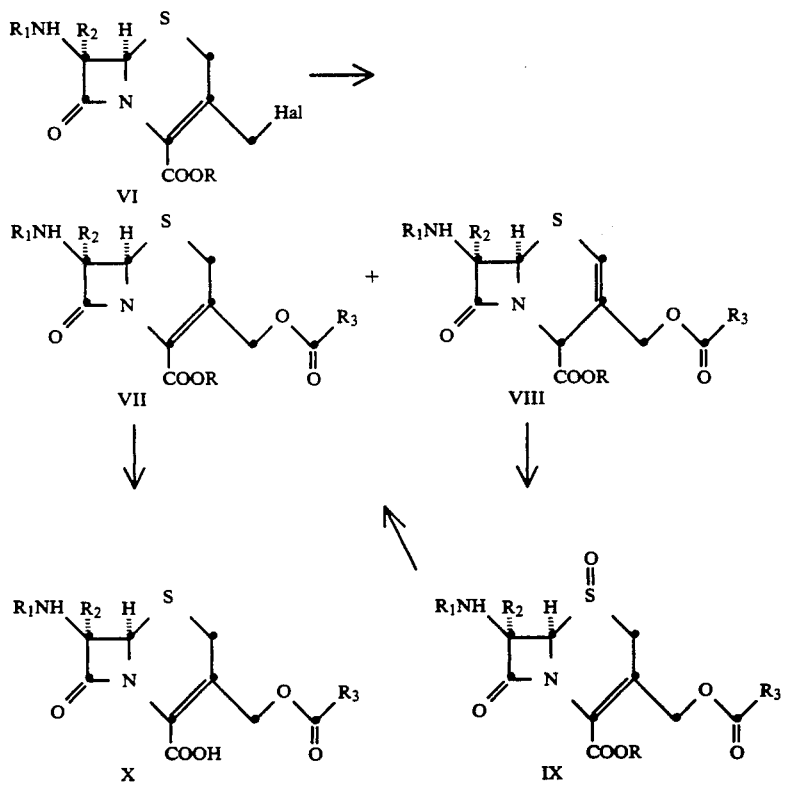

wherein $R_1$, $R_2$ and $R_3$ are as defined above.

In the above reaction scheme, depending on the carboxylic acid protecting group (R) chosen and the halogen employed, the double bond in the cephem ring may be Δ3 or Δ2 with regard to the sulfur atom due to isomerization. The mixed product may be purified, if necessary, to only the desired isomer by production of the sulfoxide (IX) and subsequent reduction of that compound or purified by separation of the two components.

Scheme I

VI→VII+VIII

The compound of formula VI, which is known or made by analogy (see, for example, U.S. Pat. No. 4,406,899 and U.S. Pat. No. 4,266,049), is reacted with the salt of the chosen carboxylic acid. The reaction is carried out in a nonhydroxylic solvent, such as dimethylformamide, methylene chloride or N,N-dimethylacetamide. Suitable salts of the carboxylic acid are, for example, sodium, potassium, cesium, silver, tetrabutylammonium, or tetramethylammonium. The preferred halogen (Hal) is bromine or iodine. The reaction is run at about 0° C. to 80° C., with about room temperature (e.g., 23°–25° C.) being preferred.

VII→X

The compound of formula VII thereafter is deprotected to obtain the desired end product of formula X using agents compatible with the ester protecting group utilized. For example, the following reagents and their corresponding compatible ester are utilized: para-nitrobenzyl removed by hydrogenolysis with palladium on carbon or by hydrolysis in the presence of sodium sulfide at about or below 0° C. to room temperature in a solvent, such as dimethylformamide (aqueous); t-butyl or diphenylmethyl ester removed by reaction with trifluoroacetic acid in the presence of anisole at about 0° C. to room temperature with or without a cosolvent, such as methylene chloride; or allyl esters removed by a palladium (O) catalyzed transallylation reaction in the presence of the sodium or potassium salt of 2-ethylhexanoic acid; see, for example, J. Org. Chem. 1982, 47, 587.

VIII⟶IX

If isomerization of the double bond occurs, the compound of formula VIII is thereafter oxidized with a peracid, such as meta-chloroperbenzoic acid, in a solvent, such as methylene chloride, at a reaction temperature of about −20° C. to 40° C., preferably at about 0° C.

IX⟶VII

The compound of formula IX is thereafter reduced to the desired end product of formula VII, utilizing one of a variety of reactions. For example, treatment with phosphorus trihalide in DMF or trifluoroacetic anhydride in the presence of sodium iodide in acetone/methylene chloride. The reaction temperature for both of the above reactions can be carried out at about 0° C. to −20° C., with about 0° C. preferred.

Scheme II

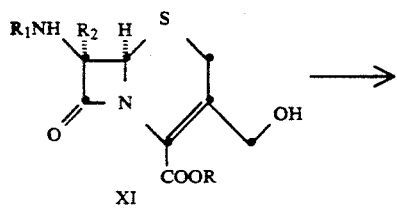

XI

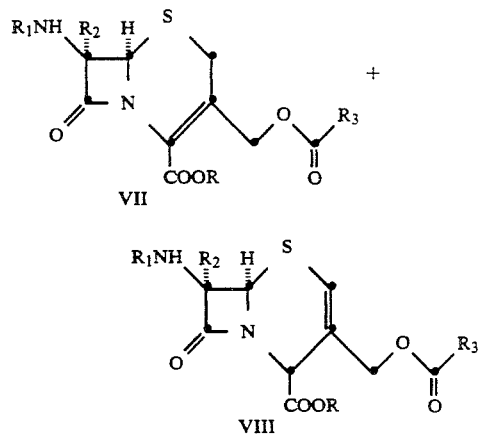

VII

VIII wherein R, $R_1$, $R_2$ and $R_3$ are defined as above.

Scheme II

XI→VII+VIII

The compound of formula XI, which is known or made by referring to the procedures described in the Journal of Antibiotics, 1981, 34, 1300, is reacted with a compound of the formula

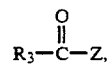

$$R_3-\overset{O}{\underset{\|}{C}}-Z,$$

where Z is an acyl activating group. Preferred for activating group Z are halogen,

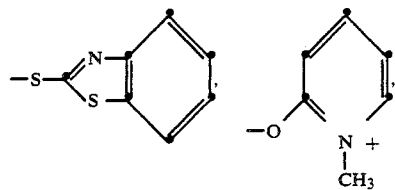

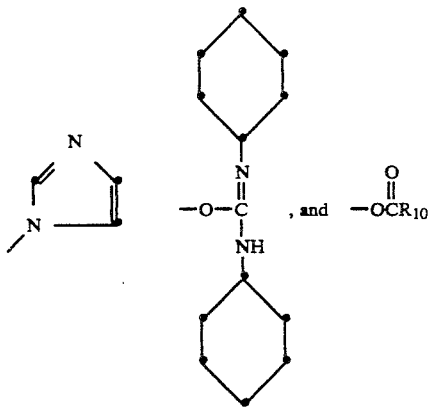

(where $R_{10}$ is $C_1$–$C_3$ alkyl).

The reaction is carried out in a solvent, such as methylene chloride, at a reaction temperature of about −20° to 100° C., preferably at about 25° C. The double bond in the cephem ring of the resulting product may be Δ3 or Δ2 with regard to the sulfur atom due to isomerization. The mixed product may be purified to only one isomer as described about for Reaction Scheme I by conventional separation or by oxidation with a peracid to form the sulfoxide (IX) and subsequent reduction of that compound to the protected ester (VII).

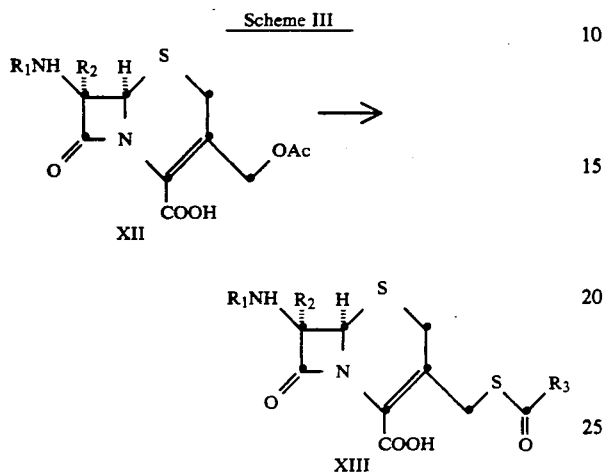

wherein $R_1$, $R_2$ and $R_3$ are as defined above and

Ac represents $CH_3\overset{O}{\underset{\|}{C}}-$

Scheme III

XII→XIII

The compound of formula XII is reacted in aqueous sodium bicarbonate with a compound of the formula

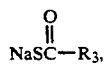

$NaS\overset{O}{\underset{\|}{C}}-R_3$, at a temperature of about 25° C. to 100° C., preferably 40° C. to 60° C., to form the desired end product (XIII).

The compound of formula XIII can also be prepared according to Reaction Scheme I in which the chosen acid is

$R_3\overset{O}{\underset{\|}{C}}SH$.

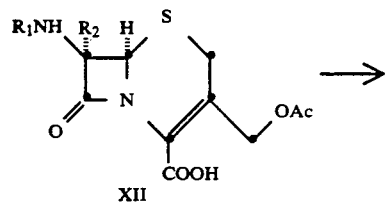

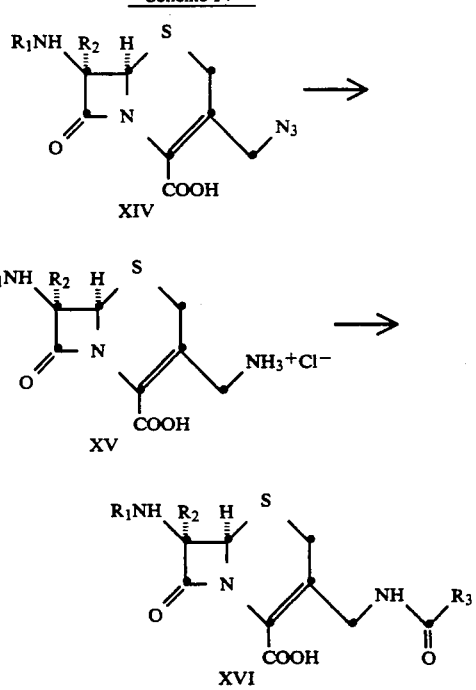

wherein Ac, $R_1$, $R_2$ and $R_3$ are as defined above.

Scheme IV

XII→XIV

The compound of formula XII is reacted with an azide salt (Na or K) in an aqueous base such as sodium bicarbonate at a temperature of about 25° to 100° C., preferably 40° to 60° C.

XIV→XV

The azide (XIV) is reduced with hydrogen and a catalyst such as palladium or platinum, or preferably with metallic tin and hydrochloric acid at a temperature of about 0° to 50° C., preferably 20° to 35° C.

XV→XVI

The amide linkage is formed by standard methods of coupling an amine with an acid as in peptide chemistry (see, for example, Synthesis, 1972, page 453, preferably using dicyclohexylcarbodiimide and N-hydroxybenzotriazole or triphenylphosphine and a diaryl disulfide, at a reaction temperature of about 0° to 50° C., preferably 20° to 35° C.

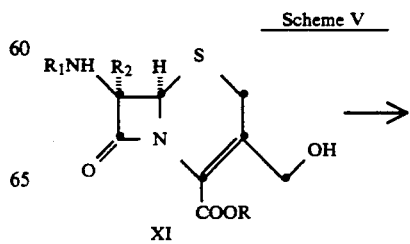

-continued
Scheme V

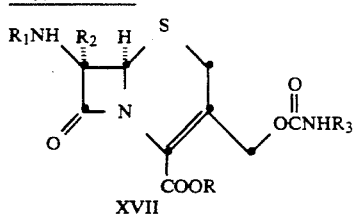

XVII wherein R, $R_1$, $R_2$ and $R_3$ are as defined above.

Scheme V

XI→XVII

The compound of formula XI is reacted with a compound of the formula O=C=N—$R_3$ or $ZCONHR_3$ with or without a base (for example, pyridine, picoline or lutidine), wherein $R_3$ is as above and Z is an acyl activating group as defined in Reaction Scheme II. The reaction is carried out in a solvent, for example, methylene chloride, at a temperature of about 0° to 60° C., and preferably at 25° C. The compound of formula XVII can thereafter be deprotected, if desired, in accordance with the procedure described for Reaction Scheme I.

In the examples which follow, chemical shifts in NMR spectra are presented as δ and band positions in infrared spectra (IR) are presented as cm$^{-1}$.

EXAMPLE 1

Preparation of [6R-[6 alpha,7beta(Z)]]-3-(acetoxymethyl)-7-amino-8-oxo-5-thia-1-azabicyclo[4.2.0]oct-2-ene-2-carboxylic acid 1,1-dimethylethyl ester To 200 ml of ice cold dioxane was added 10 ml of conc. $H_2SO_4$, followed by 21.78 g (80.0 mmol) of 7-aminocephalosporanic acid in one portion. The mixture was cooled to −50° -C., and 50 ml of liquid isobutylene (condensed separately under argon) was added. The pressure bottle was sealed and the mixture stirred overnight (approximately 18-20 psi). The mixture was then cooled to −50° -C. and the bottle was opened. The contents were poured slowly into $NaHCO_3$ (100 g in 1500 ml $H_2O$) while stirring. The solution was extracted (3×500 ml) with ethyl acetate, and the combined organic extracts were washed with brine and dried with $MgSO_4$. Removal of the solvent in vacuo gave a yellow orange oil. Trituration with petroleum ether (30–60-) gave a solid which was filtered and dried. The yield was 17.1 g (65%) and was used without further purification.

NMR ($CDCl_3$): 1.55 (S) 9H (t-bu); 2.07 (s) 3H (OAc); 3.33, 3.54 (d of d, J=10 Hz) 2H ($CH_2S$); 4.75, 5.02 (d of d, J=20 Hz) 2H ($CH_2O$); 4.72 (d, J=10 Hz) 1H (C6); 4.91 (d, J=10 Hz) 1H (C7).

EXAMPLE 2

Preparation of [6R-[6 alpha,7 beta(Z)]]-3-(acetoxymethyl)-7-[[(methoxyimino)[2-(tritylamino)-4-thiazolyl]-acetyl]amino]-8-oxo-5-thia-1-azabicyclo[4.2.0]oct-2-ene-2-carboxylic acid 1,1-dimethylethyl ester To a stirred suspension of 48 g (0.1 mole) of 2-[2-(tritylamino)thiazole-4-yl]-2-methoxyiminoacetic acid in 750 mL of anhydrous dichloromethane was added 13.94 mL (0.1 mole) of triethylamine and the mixture was mechanically stirred until a clear solution formed (approx. 45 min). After complete dissolution 20.6 g (0.1 mole) of N,N-dicyclohexylcarbodiimide and 13.5 g (0.1 mole) of 1-hydroxybenzotriazole were added and the mixture stirred at ambient temperature for 2 hours. A solution of 32.8 g (0.1 mole) of [6R-[6 alpha,7 beta(z)]]-3-(acetoxymethyl)-7-amino-8-oxo-5-thia-1-azabicyclo[4.2.0]oct-2-ene-2 carboxylic acid 1,1-dimethylethyl ester (from Example 1) in 250 mL of anhydrous dichloromethane was added and the resulting solution was stirred overnigh (16 hours) at ambient temperature. The precipitate was removed by filtration and the filtrate was washed successively with 2×250 mL=500 mL of saturated aqueous sodium bicarbonate and 2×250 mL=500 mL of saturated aqueous sodium chloride and dried over sodium sulphate. Removal of the dichloromethane afforded the crude product as a gummy-oil which was purified by preparative liquid chromatography (0–10% EtoAc in $CH_2Cl_2$), to give 57.2 g (76%) of pale yellow solid. NMR ($CDCl_3$): 1.54 (s) 9H (t-bu) 2.09 (s) 3H (OAc); 3.35, 3.56 (d of d, J=18 Hz) 2H ($CH_2S$); 4.08 (s) 3H ($OCH_3$); 4.86 5.04 (d of d, J=14 Hz) 2H ($CH_2O$); 5.04 (d, J=6 Hz) 1H (C6); 5.93 (d of d, J=6 Hz J=10 Hz), 1H (C7); 6.71 (s) 1H (thiazole); 6.91 (d, J=10 Hz) 1H (NH); 7.08 (s) 1H (NH); 7.30 (s) 15H ($CPh_3$).

EXAMPLE 3

Preparation of [6R-[6 alpha,7 beta(Z)]]-3-(iodomethyl)-7-[[(methoxyimino)[2-(tritylamino)-4-thiazolyl]-acetyl]amino]-8-oxo-5-thia-1-azabicyclo[4.2.0]oct-2-ene-2-carboxylic acid 1,1-dimethylethyl ester To a stirred solution of 23.8 g (0.0316 mole) of [6R-[6 alpha,7 beta(Z)]]-3-(acetoxymethyl)-7-[[(methoxyimino) [2-(tritylamino)-4-thiazolyl]-acetyl]amino]-8-oxo-5-thia -1-azabicyclo[4.2.0]-oct-2-ene-2-carboxylic acid 1,1-dimethylethyl ester (from Example 2) in 250 mL of anhydrous dichloromethane (distilled from $P_2O_5$) at ambient temperature was added, in three successive portions at ten minute intervals, 2.0 mL (0.014 mole) and 2.0 mL (0.014 mole) and 1.5 mL (0.0105 mole) of iodotrimethylsilane. After the last addition the mixture was stirred at room temperature for 2 hours and then a final aliquot of 0.5 mL (0.0035 mole, total amount added is 1.3 equiv.) of iodotrimethylsilane was added. After stirring for a further 30 minutes, the solvent was removed in vacuo at 0° C. (ice bath) to afford a gum which was dissolved in 250 mL of ethyl acetate (precooled to 0° C.). The ethyl acetate solution was washed (all solutions were precooled to about 0° C.) successively with 3×125 mL=375 mL of cold 10% aqueous sodium thiosulfate, 125 mL of saturated aqueous sodium bicarbonate, 2×125 mL of saturated aqueous sodium chloride and dried over anhydrous sodium sulfate. The solvent was removed in vacuo at 0° C. to afford a gum which was purified immediately preparative liquid chromatography (EtoAc/hexane/methylenechloride, 1:4:6), to give the desired iodomethylcephalosporin, (15.4 g, 59%) as a pale yellow solid. Unreacted starting material (5.0 g) was also recovered and so the yield based on reacted starting material is 75%.

NMR ($CDCl_3$): 1.56 (s) 9H (t-bu); 3.51, 3.76 (d of d, J=20 Hz) 2H ($CH_2S$); 4.11 (s) 3H ($OCH_3$); 4.30, 4.44 (d of d, J=10 Hz) 2H ($CH_2I$); 5.03 (d, J=6 Hz) 1H (C6); 5.89 (d of d, J=6 Hz, J=10 Hz) 1H (C7); 6.72 (m) 2H (thiazole, NH), 7.02 (s) 1H (NH); 7.30 (s) 15H ($CPh_3$). IR (KBr): 3385, 3285, 1787, 1717, 1681, 1524, 701.

EXAMPLE 4

Preparation of [6R-[6 alpha,7 beta(Z)]]-3-[[(3,4-bis(acetyloxy)benzoyl)oxy]methyl]-8-oxo-7-[[[2-[(triphenylmethyl)amino]-4-thiazolyl](methoxyimino)acetyl]-amino]-5-thia-1-azabicyclo[4.2.0]oct-2-ene-2-carboxylic acid 1,1-dimethylethyl ester To a solution of 6.98 g (0.085 mole of [6R-[6-α,7β(Z)[[3-(iodomethyl)-7-[[[(methoxyimino)-2-[(triphenylmethyl)amino]-4-thiazolyl]acetyl]amino]-8-oxo-5-thia-1-azabicyclo[4.2.0]oct-2-ene-2-carboxylic acid 1,1-dimethylethyl ester (from Example 3) in 100 mL of dry DMF was added dropwise a stirred solution of 2.29 g (0.088 mole) of sodium (3,4-diacetoxy)benzoate in 100 mL of dry DMF (previously dried for 1 hour over 4A molecular sieves) under argon at ambient temperature. The reaction mixture was stirred for 3 hours and the solvent removed in vacuo. The oily residue was dissolved in 100 mL of $CH_2Cl_2$/EtOAc (9:1) and passed through a short silica gel column. The appropriate fractions were combined to give 7.25 g of crude material. Further purification using preparative chromatography (hexane/EtOAc, 5:4) gave 3.9 g (42%) of a cream colored solid.

NMR ($CDCl_3$): 1.44 (s) 9H (t-bu); 2.27 (s) 3H (OAc); 2.29 (s) 3H (OAc) 3.63 3.73 (d of d, J=20 Hz)2H ($CH_2S$); 3.81 (s) 3H ($OCH_3$); 4.91, 5.19 (d of d, J=16 Hz) 2H ($CH_2O$); 5.13 (d J=6 Hz) 1H (C6); 5.99, 6.01 (d of d, J=6 Hz, J=10 Hz) 1H (C7); 6.68 (s) 1H (thiazole) 7.2–7.4 (m) 15H ($CPh_3$); 7.44 (d, J=9 Hz) 1H (Ar); 7.84 (s) 1H (Ar); 7.91 (d, J=9 Hz) 1H (Ar); 8.86 (s) 1H (NH); 9.59 (d, J=10 Hz) 1H (NH). I.R. (KBr); 3300, 1778, 1772, 1682. U.V. (EtOH): λ max 234 (ε=36,500); M.S.: m/z 932 (M=H).

EXAMPLE 5

Preparation of [6R-[6 alpha,7 beta(Z)]]-3-[[(3,4-dihydroxybenzoyl)oxy]methyl]-8-oxo-7-[[[2-[(triphenylmethyl)amino]-4-thiazolyl](methoxyimino)acetyl]amino]-5-thia-1-azabicyclo[4.2.0]oct-2-ene-2-carboxylic acid 1,1-dimethylethyl ester By following the procedures and conditions described in Example 4, 374 mg (2.12 mmol) of sodium 3,4-dihydroxy benzoate in 80 mL of DMF added to 1.65 g (2.0 mml) of [6R-[6α,7β(Z)]]-3-(iodomethyl)-7-[[[(methoxyimino)-2-[(triphenylmethyl)amino]-4-thiazolyl]acetyl]amino]-8-oxo-5-thia-1-azabicyclo[4.2.0]oct-2-ene-2-carboxylic acid 1,1-dimethylethyl ester in 50 mL of DMF followed by stirring for 1.5 hours, gave 1.71 g (50%) of a cream colored solid after silica gel chromatography (99:1 $CH_2Cl_2$/MeOH).

NMR ($CDCl_3$): 1.22 (s) 9H (t-bu); 3.30, 3.54 (d of d, J=16 Hz) 2H ($CH_2S$); 3.82 (s) 3H ($OCH_3$); 4.04 (br s) 2H (OH); 5.07 (d, J=6 Hz) 1H (C6); 5.24, 5.32 (d of d, J=12 Hz) 2H ($CH_2O$); 5.95 (d of d, J=6 Hz, J=10 Hz) 1H (C7); 6.77 (s) 1H (thiazole); 6.87 (d, J=10 Hz) 1H (Ar); 7.30 (s) 15H ($CPh_3$); 7.49 (m) 3H (Ar). I.R. (KBr): 3290, 1791, 1690, 1522, 702. U.V. (EtOH): λ max 260 nm (δ=23,200); M.S.: m/z 848 (M+H).

EXAMPLE 6

Preparation of [6R-[6 alpha, 7 beta(Z)]]-3-[[(2,3-dihydroxybenzoyl)oxy]-methyl]-8-oxo-7-[[[2-[(triphenylmethyl)amino]-4-thiazolyl](methoxyimino)-acetyl]amino]-5-thia-1-azabicyclo[4.2.0]oct-2-ene-2-carboxylic acid 1,1-dimethylethyl ester By following the procedures and conditions described in Example 4, 35.3 mg (0.20 mmol) of sodium 2,3-dihydroxybenzoate in 5 mL of DMF added to 157 mg (0.19 mml) of [6R-[6α,7β(Z)]]-3-(iodomethyl)-7-[[[(methoxyimino)-2-[(triphenylmethyl)amino]-4-thiazolyl]acetyl]amino]-8-oxo-5-thia-1-azabicyclo[4.2.0]-oct-2-ene-2-carboxylic acid 1,1-dimethylethyl ester in 5 mL of DMF, followed by stirring for 2 hours, 15 minutes, gave 111 mg (69%) of an off-white solid after silica gel chromatography (0–10% EtoAc in $CH_2Cl_2$).

NMR ($CDCl_3$): 1.59 (s) 3H (t-bu); 3.48, 3.68 (d of d, J=20 Hz) 2H ($CH_2S$); 4.07 (s) 3H ($OCH_3$); 5.10 (m) 2H (C6, ½$CH_2O$); 5.48 (d, J=14 Hz) 1H (½$CH_2O$); 5.99 (m) 1H (C7); 6.67 (br s) 1H (OH) 6.72–6.88 (m) 3H (thiazole, 2 Ar) 7.02 (br s) 1H; 7.16 (d of d, J=10 Hz) 1H (NH) 7.28 (s) 15H ($CPh_3$); 10.71 (s) 1H (OH). I.R. (KBr): 3400, 1789, 1722, 1688, 700. U.V. (EtOH): λ max 240 nm (ε=33,900); MS: m/z 848 (M+H).

EXAMPLE 7

Preparation of [6R-[6 alpha,7 beta(Z)]]-3-[[(3,4,5-tris (acetyloxy)benzoyl)oxy]-methyl]-7-[[[(methoxyimino)[2-(triphenylmethyl)amino]-4-thiazolyl]acetyl]amino]-8-oxo-5-thia-1-azabicyclo[4.2.0]oct-2-ene-2-carboxylic acid-1,1-dimethylethyl ester By following the procedures and conditions described in Example 4, 59 mg (0.195 mmol) of sodium 3,4,5-triacetoxy benzoate in 2 mL of DMF added to 160.8 mg of [5R-[5α, 7β(Z)]]-3-(iodomethyl)-7-[[[(methoxyimino)-2-[(triphenylmethyl)amino]-4-thiazolyl]acetyl]amino]-8-oxo-5-thia-1-azabicyclo[4.2.0]oct-2-ene-2-carboxylic acid 1,1-dimethylethyl ester in 2 mL of DMF, followed by stirring for 2 hours, gave 64.1 mg (33%) of a cream colored solid after silica gel chromatography (0–15% EtoAc in $CH_2Cl_2$).

NMR ($CDCl_3$): 1.52 (s) 9H (t-bu); 3.37, 3.59 (d of d, J=18 Hz) 2H ($CH_2S$); 4.06 (s) 3H ($OCH_3$); 5.02, 5.38 (d of d, J=14 Hz) 2H ($CH_2O$); 5.05 (d, J=6 Hz) 1H (C6); 5.95 (d of d, J=6 Hz, J=10 Hz) 1H (C7); 6.70 (d, J=10 Hz) 1H (NH); 6.72 (s) 1H (thiazole); 6.98 (s) 1H (NH); 7.29 (s) 15H ($CPh_3$); 7.77 (s) 2H (Ar). IR (KBr): 3340, 1788, 1722, 1690, 701. U.V. (EtOH): λ max 235 nm (ε=32,750); M.S.: m/z 990 (M+H).

EXAMPLE 8

Preparation of [6R-[6 alpha,7 beta(Z)]]-3-[[2-(3,4-dihydroxyphenyl) oxoethoxy]methyl]-7-[[[(methoxyimino)-2-[(triphenylmethyl)amino]-4-thiazolyl]acetyl]amino]-8-oxo-5-thia-1-azabicyclo[4.2.0]oct-2-ene-2-carboxylic acid 1,1-dimethylethylester By following the procedures and conditions described in Example 4, 76 mg (0.400 mmol) of 2-(3,4-dihydroxyphenyl) acetic acid sodium salt in 4.0 mL of DMF added to 328.7 mg (0.400 mmol) of [6R-[6α, 7β(Z)]]-3-(iodomethyl)-7-[[[(methoxyimino)-2-[(triphenylmethyl)amino]-4-thiazolyl]acetyl]amino]-8-oxo-5-thia-1-azabicyclo[4.2.0]oct-2-ene-2-carboxylic acid 1,1-dimethylethyl ester in 4 mL of DMF, followed by stirring for 2 hours 30 minutes, gave 215 mg (62%) of a cream colored solid after silica gel chromatography (0–20% EtoAc in CH$_2$Cl$_2$).

NMR (DMSO-d$_6$): 1.44 (s) 9H (t-bu); 3.23–3.45 (m) 4H (CH$_2$S, CH$_2$CO); 3.80 (s) 3H (OCH$_3$); 4.65, 4.95 (d of d, J=14 Hz) 2H (CH$_2$O); 5.11 (d, J=4 Hz) 1H (C6); 5.69 (d of d, J=4 Hz, J=10 Hz) 1H (C7); 6.46–6.65 (m) 3H (Ar); 6.69 (s) 1H (thiazole); 7.19–7.37 (m) 15H (CPh$_3$); 8.80 (s) 1H (OH); 8.86 (s) 1H (NH); 6.88 (s) 1H (OH); 9.57 (d, J=10 Hz) 1H (NH). IR (KBr): 3390, 1788, 1723, 1662, 702. U.V. (EtOH): λ max 225 nm (ε=19,900); M.S.: m/z 861 (M+H).

EXAMPLE 9

Preparation of (6R-trans)-3-[[[(3,4-bis(acetyloxy)benzoyl]oxy]methyl]-8-oxo-7-[(phenoxyacetyl)amino]-5-thia-1-azabicyclo[4.2.0]oct-2-ene-2-carboxylic acid 1,1-dimethylethyl ester By following the procedures and conditions described in Example 4, 2.33 g (8.95 mmol) of sodium 3,4-diacetoxybenzoate in 100 mL of DMF added to 4.75 g (8.95 mmol) of (6R-trans)-3-(iodomethyl)-8-oxo-7-[(phenoxyacetyl)amino]-5-thia-1-azabicyclo[4.2.0]oct-2-ene-2-carboxylic acid 1,1-dimethylethyl ester in 50 mL of DMF, followed by stirring for 2 hours, gave 3.36 g (58.5%) of a cream colored solid after silica gel chromatography (6:4 hexane/EtOAc).

NMR (CDCl$_3$): 1.56 (s) 9H (t-bu); 2.33 (s) (6H) (2 OAc); 3.41, 3.63 (d of d, J=18 Hz) 2H (CH$_2$S); 4.60 (s) 3H (OCH$_3$); 5.06, 5.40 (d of d, J=14 Hz) 2H (CH$_2$O); 5.07 (d, J=6 Hz) 1H (C6); 5.97 (d of d, J=6 Hz, J=10 Hz) 1H (C7); 6.98 d J=8 Hz) 1H (Ar); 7.09 (d, J=10 Hz) 1H (NH); 7.12–7.40 (m) 5H (Ar); 7.90 (s) 1H (Ar); 7.98 (d, J=8 Hz) 1H (Ar).

EXAMPLE 10

Preparation of [6R-[6 alpha,7 beta(Z)]]-7-[[(2-amino-4-thiazolyl) (methoxyimino) acetyl]amino]-3-[[[(3,4-bis (acetyloxy)benzoyl)]oxy]methyl]-8-oxo-5-thia-1-azabicyclo [4.2.0]oct-2-ene-2-carboxylic acid monosodium salt A solution of 1.90 g (2.04 mmol) of [6R-[6 alpha,7 beta(Z)]]-3-[[[3,4-bis(acetyloxy)benzoyl]oxy]-methyl]-8-oxo-7-[[[2-[(triphenylmethyl)amino]-4-thiazolyl](methoxyimino)acetyl]amino]-5-thia-1-azabicyclo[4.2.-0]oct-2-ene-2-carboxylic acid 1,1-dimethylethyl ester (from Example 4) in 38 mL of dry methylene chloride was cooled to 0° C. in a ice/water bath and treated with 3.8 mL of anisole followed by 37.5 ml of trifuloroacetic acid. The reaction mixture was stirred at 0° C. for 6 hours, and the volatiles were removed in vacuo. The residual oil was taken up in 40 mL ethyl acetate and washed with 9 portions (40 mL each) of 1% aqueous sodium bicarbonate. Fractions 4–7, containing the UV-active materials, were combined and passed through a short column of C$_{18}$ reverse phase silica gel, using water to remove the excess NaHCO$_3$, followed by 25% acetonitrile in water to remove the organic material. The appropriate fractions were combined and lyophylized to give 760 mg of crude material. The lyophylized powder was further purified using preparative reverse phase chromatography (0–30% CH$_3$CN) to give 580 mg (43%) of a white powder.

NMR (DMSO-d$_6$): 2.29 (s) 3H (OAc); 2.30 (s) 3H (OAc); 3.26, 3.60 (d of d, J=16 Hz) 2H (CH$_2$S) 3.84 (s) 3H (OCH$_3$); 4.95, 5.21 (d of d, J=10 Hz) 2H (CH$_2$O); 4.97 (d, J=6 Hz) 1H (C6); 5.53 (d of d, J=6 Hz, J=10 Hz) 1H (C7); 6.69 (s) 1H (thiazole); 7.19 (s) 1H (NH), 7.39 (d, J=8 Hz) 1H (Ar); 7.80 (s) 1H (Ar) 7.87 (d, J=8 Hz) 1H (Ar); 9.51 (d, J=8 Hz) 1H (NH). IR (KBr): 3350, 1769, 1715, 1685, 1610; MS: m/z 656 (M+H) UV (H$_2$O): λ max=235 nm (ε=26,500). HRMS calc. (M+H) for C$_{25}$H$_{23}$NaN$_5$O$_{11}$S$_2$: 656.0733. Found: 656.0732.

EXAMPLE 11

Preparation of [6R-[6 alpha, 7 beta(Z)]]-7-[[(2-amino-4-thiazolyl) (methoxyimino)acetyl]amino]-3-[[[(3,4-dihydroxyphenyl)carbonyl]oxy]methyl]-8-oxo-5-thia-1-azabicyclo[4.2.0]oct-2-ene-2-carboxylic acid monosodium salt By following the procedures and conditions described in Example 10, 52.3 mg (0.092 mmol) of [6R-[6 alpha,7 beta(Z)]]-3-[[(3,4-dihydroxybenzoyl)oxy]methyl]-8-oxo-7-[[[2-[(triphenylmethyl)amino]-4-thiazolyl](methoxyimino)acetyl]amino]-5-thia-1-azabicyclo[4.2.0]oct-2-ene-2-carboxylic acid 1,1-dimethylethyl ester (Example 5) in 1 mL of CH$_2$Cl$_2$ and 100 μL of anisole, treated with 1 mL of TFA, followed by stirring for 3 hours 40 minutes, gave 11.3 mg (32%) of a white powder after reverse phase chromatography (0–30% CH$_3$CN in H$_2$O).

NMR (D$_2$O): 3.47, 3.73 (d, J=18 Hz) 2H (CH$_2$S); 3.98 (s) 3H (OCH$_3$); 4.89, 5.11 (d of d, J=10 Hz) 2H (CH$_2$O); 5.21 (d, J=6 Hz) 1H (C6); 5.80 (d, J=6 Hz) 1H (C7); 6.91 (d, J=8 Hz) 1H (Ar); 7.00 (s) 1H (thiazole); 7.48 (s) 1H (Ar); 7.52 (d, J=8 Hz) 1H (Ar). IR (KBr): 3320, 1762, 1680, 1610, 1530. MS: m/z 572 (M+H). UV (H$_2$O): λ max=260 nm (ε=21,800). HRMS calc. (M+H) for C$_{21}$H$_{19}$NaN$_5$O$_9$S$_2$: 572.0522. Found: 572.0533.

EXAMPLE 12

Preparation of [6R-trans)-3-[[[3,4-bis(acetyloxy)benzoyl]oxy]methyl]-8-oxo-7-[(phenoxyacetyl)amino]-5-thia-1-azabicyclo [4.2.0] oct-2-ene-2-carboxylic acid monosodium salt By following the procedures and conditions described in Example 10, 129 mg (0.201 mmol) of (6R-trans)-3-[[[3,4-bis (acetyloxy)benzoyl]oxy]methyl]-8-oxo-7-[(phenoxyacetyl)amino]-5-thia-1-azabicyclo[4.2.-0]oct-2-ene-2-carboxylic acid 1,1-dimethylethyl ester (Example 9) in 2.5 mL CH$_2$Cl$_2$ and 220 μL of anisole, treated with 2.2 mL of TFA, followed by stirring for 6 hours and 30 minutes, gave 42 mg (34%) of a white powder after reverse phase chromatography (0–30% CH$_3$CN in H$_2$O).

NMR (D$_2$O): 2.37 (s) 6H (2 OAc); 3.42, 3.70 (d of d, J=18 Hz) 2H (CH$_2$S); 4.96, 5.16 (d of d, J=12 Hz) 2H (CH$_2$OCO); 5.11 (d, J=6 Hz) 1H (C6); 6.70 (d, J=6 Hz) 1H (C7); 7.01 (d, J=8 Hz) 1H (Ar); 7.05 (M) 1H (Ar) 7.32–7.43 (m) 4H (Ar) 7.92 (s) 1H (Ar) 8.00 (d, J=8 Hz) 1H (Ar) (CH$_2$OAr obscured by HOD). IR (KBr): 3450, 1782, 1718, 1692, 1608. MS: m/z 607 (M+H). UV (H$_2$O): λmax=236 nm (ε=13,400). HRMS calc. (M+H) for C$_{27}$H$_{24}$NaN$_2$O$_{11}$S$_2$: 607.0999. Found: 607.1007.

EXAMPLE 13

Preparation of [6R-[6 alpha,7 beta(Z)]]-7-[[(2-amino-4-thiazolyl)(methoxyimino)acetyl]amino]-3-[[[(2,3-dihydroxyphenyl)carbonyl]oxy]methyl]-8-oxo-5-thia-1-azabicyclo[4.2.0]oct-2-ene-2-carboxylic acid monosodium salt By following the procedures and conditions described in Example 10, 100 mg (0.118 mmol) of [6R-[6 alpha,7 beta(Z)]]-3-[[(2,3-dihydroxybenzoyl)oxy]methyl]-8-oxo-7-[[[2-[(triphenylmethyl)amino]-4-thiazolyl](methoxyimino)acetyl]amino]-5-thia-1-azabicyclo[4.2.0]oct-2-ene-2-carboxylic acid 1,1-dimethylethyl ester (Example 6) in 3.0 mL of $CH_2Cl_2$ and 300 µL of anisole, treated with 3.0 mL of TFA, followed by stirring for 6 hours, gave 28.2 mg (42%) of a white powder after reverse phase chromatography (0–30% $CH_3CN$ in $H_2O$).

NMR ($D_2O$): 3.30, 3.57 (d of d, J = 16 Hz) 2H ($CH_2S$); 3.78 (s) 3H ($OCH_3$); 4.78, 5.02 (d of d, J = 12 Hz) 2H ($CH_2OCO$); 5.04 (d, J = 6 Hz) 1H (C6); 5.66 (d, J = 6 Hz) 1H (C7); 6.64 (m) 1H (Ar); 6.81 (s) 1H (thiazole); 6.91 (d, J = 8 Hz) 1H (Ar); 7.24. (d, J = 6 Hz) 1H (Ar). IR (KBr): 3350, 1765, 1672, 1612. MS: m/z 572 (M+H). UV ($H_2O$): λmax 245 nm ($\epsilon$ = 21,400), λmax 298 nm ($\epsilon$ = 8600). HRMS calc. (M+H) for $C_{21}H_{19}NaN_5O_9S_2$: 572.0522. Found: 572.0505.

EXAMPLE 14

Preparation of [6R-[6 alpha,7 beta(Z)]]-3-[[3,4,5-tris(acetyloxy)benzoyl]oxy]-methyl]-7-[[(2-amino-4-thiazolyl)(methoxyimino)acetyl]amino]-8-oxo-5-thia-1-azabicyclo[4.2.0]oct-2-ene-2-carboxylic acid monosodium salt By following the procedures and conditions described in Example 10, 160 mg (0.161 mmol) of [6R-[6 alpha,7 beta(Z)]]-3-[[3,4,5-tris(acetyloxy)benzoyl]oxy]-methyl]-7-[[(methoxyimino)[2-[(triphenylmethyl)amino]-4-thiazolyl]acetyl]amino]-8-oxo-5-thia-1-azabicyclo[4.2.0]oct-2-ene-2-carboxylic acid 1,1-dimethylethyl ester (Example 7) in 3.2 mL of $CH_2Cl_2$ and 300 µL of anisole, treated with 3.0 mL of TFA, followed by stirring for 6 hours 30 minutes, gave 69 mg (60%) of a white solid after reverse phase chromatography (0–30% $CH_3CN$ in $H_2O$).

NMR ($D_2O$): 2.38 (S) 3H (OAc); 2.39 (s) 3H (OAc); 3.51, 3.78 (d of d, J = 16 Hz) 2H ($CH_2S$); 5.00, 5.21 (d of d, J = 12 Hz) 2H ($CH_2O$); 5.24 (d, J = 6 Hz) 1H (C6); 5.82 (d, J = 6 Hz) 1H (C7); 7.03 (s) 1H (thiazole); 7.79 (s) 2H (Ar). IR (KBr): 3360, 1772, 1718, 1675, 1610. MS: m/z 714 (M+H). UV ($H_2O$): λmax = 234 nm ($\epsilon$ = 18,100). HRMS calc. (M+H) for $C_{27}H_{25}NaN_5O_{13}S_2$: 714.0788. Found: 714.0745.

EXAMPLE 15

Preparation of [6R-[6 alpha,7 beta(Z)]]-7-[[(2-amino-4-thiazolyl)(methoxyimino)acetyl]amino]-3-[[2-(3,4-dihydroxyphenyl)-1-oxoethoxyl]methyl]-8-oxo-5-thia-1-azabicyclo[4.2.-0]oct-2-ene-2-carboxylic acid monosodium salt By following the procedures and conditions described in Example 10, 175 mg (0.203 mmol) of [6R-[6 alpha,7 beta(Z)]]-3-[[[2-(3,4-dihydroxyphenyl)-1-oxoethoxyl]methyl]-7-[[(methoxyimino)[2-[(triphenylmethyl)amino]-4-thiazolyl]acetyl]amino]-8-oxo-5-thia-1-azabicyclo[4.2.0]oct-2-ene-2-carboxylic acid 1,1-dimethylethyl ester (Example 8) in 3.5 mL of $CH_2Cl_2$ and 350 µL of anisole, treated with 3.5 mL of TFA, followed by stirring for 6 hours, gave 22 mg (19%) of a while solid after reverse phase chromatography (0–30% $CH_3CN$ in $H_2O$). NMR ($D_2O$): 3.27, 3.49 (d of d, J = 16 Hz) 2H ($CH_2S$); 3.62 (s) 2H ($CH_2O$); 4.00 (s) 3H ($OCH_3$); 5.00 (d, J = 12 Hz) 1H (½$CH_2O$) (other doublet obscured by HOD); 5.17 (d, J = 6 Hz) 1H (C6); 5.82 (d, J = 6 Hz) 1H (C7); 6.75 (d, J = 8 Hz) 1H (Ar); 6.86 (s) 1H (Ar); 6.90 (d, J = 8 Hz) 1H (Ar); 7.04 (s) 1H (thiazole). IR (KBr): 3340, 1763, 1670, 1610. MS: m/z 586 (M+H), 564 (M+H free acid). UV ($H_2O$) sh 230 nm ($\epsilon$ = 16,900), sh 260 nm ($\epsilon$ = 13,300). HRMS calc. (M+H) for $C_{22}H_{21}NaN_5O_9S_2$: 586.0678. Found: 586.0641.

EXAMPLE 16

Preparation of (6R-trans)-7-amino-3-[[[3,4-bis-(acetyloxy)benzoyl]oxy]methyl]-8-oxo-5-thia-1-azabicyclo[4.2.0]oct-2-ene-2-carboxylic acid 1,1-dimethylethyl ester monohydrochloride A solution of 1.66 mL (20.0 mmol) of pyridine in 60 mL of dry $CH_2Cl_2$ under argon was cooled to 0° C. in an ice-water bath and treated with 4.16 g (20.0 mmol) of $PCl_5$. The mixture was stirred at 0° C. for 45 minutes. To this was added dropwise a solution of 8.80 g of (6R-trans)-3-[[[3,4-bis(acetyloxy)benzoyl]oxy]methyl]-8-oxo-7-[(phenoxyacetyl)amino]-5-thia-1-azabicyclo[4.2.0]oct-2-ene-2-carboxylic acid 1,1-dimethylethyl ester (Example 9) in 40 mL of dry $CH_2Cl_2$ over 20 minutes. The reaction was stirred at 0° C. for 1 hour 30 minutes, followed by the addition of 24 mL of 1-propanol added dropwise. Stirring was continued for 1 hour, and then treated with 60 mL $H_2O$, and stirred for 40 minutes. The volatiles were removed under reduced pressure. The remaining aqueous solution was treated with 300 µmL of $Et_2O$ while stirring vigorously to precipitate the product as a white crystalline solid 5.28 g (71%).

NMR (DMSO-$d_6$): 1.49 (s) 9H (t-bu); 2.32 (s) 3H (OAc); 2.33 (s) 3H (OAc); 3.78. 3.87 (d of d, J = 18 Hz) 2H ($CH_2S$); 4.97 (m) 1H (C6); 5.24 (m) 3H (C7, $CH_2O$); 7.47 (d, J = 8 Hz) 1H (Ar); 7.85 (s) 1H (Ar); 7.92 (d, J = 8 Hz) 1H (Ar); 9.05 (br) 3H ($NH_3+$). IR (KBr): 3400, 1778, 1772. UV (EtOH): λmax 238 nm ($\epsilon$ = 15,580).

EXAMPLE 17

Preparation of [6R-[6 alpha,7 beta(Z)]]-3-[[[3,4-bis(acetyloxy)benzoyl]oxy]-methyl]-7-[[[(2-amino-4-thiazolyl)[1,1-dimethyl-2-(1,1-dimethylethoxy)-2-oxoethoxy]imino]acetyl]amino]-8-oxo-5-thia-1-azabicyclo[4.2.0]oct-2-ene-2-carboxylic acid 1,1-dimethylethyl ester A suspension of 1.00 g (1.84 mmol) of (6R-trans)-7-amino-3-[[[3,4-bis(acetyloxy)benzoyl]oxy]methyl]-8-oxo-5-thia-1-azabicyclo[4.2.0]oct-2-ene-2-carboxylic acid 1,1-dimethylethyl estermonohydrochloride (Example 16) in 25 mL $CH_2Cl_2$ was washed thoroughly with 25 mL of a brine/saturated sodium bicarbonate mixture (4:1). The organic solution was separated and dried over $MgSO_4$. To this solution was added in one portion 1.10 g (2.30 mmol) of S-2-benzothiazolyl 2-amino-alpha-[(Z)-[1-(tertbutoxycarbonyl)-1-methylethoxy]imino]thio-4-thiazole acetate. The resulting solution was stirred for 16 hours and the solvent removed in vacuo. The residue was chromatographed on silica gel using hexane/ethyl acetate (1:1), then ethyl acetate, as elutants to give 1.16 g (77%) of a cream colored solid.

NMR (CDCl$_3$): 1.41 (s) 9H (t-bu); 1.52 (s) 9H (t-bu); 1.56 (s) 3H (CH$_3$); 1.58 (s) 3H (CH$_3$); 2.29 (s) 6H (2OAc); 3.38, 3.59 (d of d, J=18 Hz) 2H (CH$_2$S); 5.04 (m) 2H (C6, ½CH$_2$O); 5.38 (d, J=12 Hz) 1H (½CH$_2$O); 6.01 (d of d, J=6 Hz, J=10 Hz) 1H (C7); 6.10 (s) 2H (NH$_2$); 6.88 (s) 1H (thiazole); 7.25 (d, J=12 Hz) 1H (NH); 7.68 (d, J=8 Hz) 1H (Ar), 7.82 (s) 1H (Ar); 7.91 (d, J=8 Hz) 1H (Ar). IR (KBr): 3300, 1782, 1722, 1688, 1535. MS: m/z 818 (M+H). UV (EtOH) λmax 235 nm (ε=28,450).

EXAMPLE 18

Preparation of [6R-[6 alpha,7 beta(Z)]]-3-[[[3,4-bis(acetyloxy)benzoyl]oxy]-methyl]-7-[[[2-amino[(2-amino-2-oxoethoxy)imino]-4-thiazolyl]acetyl]amino]-8-oxo-5-thia-1-azabicyclo[4.2.0]oct-2-ene-2-carboxylic acid 1,1-dimethylethyl ester A suspension of 234 mg (0.430 mmol) of (6R-trans)-7-amino-3-[[[3,4-bis(acetyloxy)benzoyl]oxy]methyl]-8-oxo-5-thia-1-azabicy[4.2.0]oct-2-ene-2-carboxylic acid 1,1-dimethylethyl ester monohydrochloride in 10 mL CH$_2$Cl$_2$ was washed with 10 mL of a brine/saturated NaHCO$_3$ (4:1). The organic solution was separated and dried with MgSO$_4$. This solution was added dropwise to a solution of 157 mg (0.400 mmol) of S-(2-benzothiazolyl)-Z-aminothio-4-thiazole-glyoxylate O-(carbamoylmethyl)oxime in 5 mL of CH$_2$Cl$_2$ and 8 mL of dry DMF. Stirring was continued for 3 hours and the solvents were removed in vacuo. The residue was chromatographed (O-10% MeOH in CH$_2$Cl$_2$) to give 220 mg (70%) of a cream colored material.

NMR (CDCl$_3$): 1.51 (s) 9H (t-bu); 2.28 (s) 3H (OAc); 2.29 (s) 3H (OAc); 3.48, 3.51 (d of d, J=18 Hz) 2H (CH$_2$S); 4.60, 4.81 (d of d, J=18 Hz) 2H (CH$_2$CON); 4.96, 5.37 (d of d, J=12 Hz) 2H (CH$_2$O); 5.10 (d, J=6 Hz) 1H (C6); 5.83 (br) 2H (NH$_2$) 5.83 (br) 2H (NH$_2$) 6.01 (d of d, J=6 Hz, J=10 Hz) 1H (C7); 6.76 (s) 1H (thiazole); 7.27 (d, J=8 Hz) 1H (Ar); 7.85 (s) 1H (Ar); 7.93 (d, J=8 Hz) 1H (Ar). IR (KBr): 3450, 3350, 1778, 1720, 1680, 1532. MS: m/z 733 (M+H). UV (EtOH) λmax 236 nm (ε=29,700).

EXAMPLE 19

Preparation of [6R-[6 alpha,7 beta(Z)]]-3-[[[3,4-bis(acetyloxy)benzoyl]oxy]methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid disodium salt By following the procedures and conditions described in Example 10, 247 mg (0.301 mmol) of [6R-[6 alpha,7 beta(Z)]]-3-[[[3,4-bis(acetyloxy)benzoyl]oxy]methyl]-7-[[[(2-amino-4-thiazolyl)[1,1-dimethyl-2-(1,1-dimethylethoxy)-2-oxoethoxy]imino]acetyl]amino]-8-oxo-5-thia-1-azabicyclo[4.2.0]-oct-2-ene-2-carboxylic acid 1,1-dimethylethyl ester (Example 17) in 2.5 mL of CH$_2$Cl$_2$ and 250 μL of anisole, treated with 2.5 mL of TFA, followed by stirring for 7 hours, gave 61.2 mg (27%) of a white solid after reverse phase chromatography (0-30% CH$_3$CN in H$_2$O).

NMR (DMSO-d$_6$): 1.30 (s) 3H (CMe$_2$); 1.37 (s) 3H (CMe$_2$); 2.20 (s) 3H (OAc); 2.21 (s) 3H (OAc); 3.49 (d, J=18 Hz) 1H (½CH$_2$S, other half obscured by HOD); 4.87, 5.23 (d of d, J=12 Hz) 2H (CH$_2$O); 4.96 (d J=6 Hz) 1H (C6); 5.60 (d of d, J=6 Hz, J=10 Hz) 1H (C7); 6.66 (s) 1H (thiazole); 7.11 (br) 3H (NH, NH$_2$); 7.37 (d, J=8 Hz) 1H (Ar); 7.78 (s) 1H (Ar); 7.85 (d, J=8 Hz) 1H (Ar). IR (KBr): 3400, 1770, 1718, 1672, 1608. MS: m/z 650 (M+H). UV (EtOH): λmax 235 nm (ε=20,000).

HRMS calc. (M+H) for C$_{28}$H$_{25}$NaN$_5$O$_{13}$S$_2$: 772.0584. Found: 772.0543.

EXAMPLE 20

Preparation of [6R-[6 alpha,7 beta(Z)]]-7-[[[(2-amino-4-thiazolyl)[1-carboxy-1-methylethoxy]imino]acetyl]amino]-3-[[(3,4-dihydroxybenzoyl)oxy]methyl]-8-oxo-5-thia-1-azabicyclo[4.2.0]oct-2-ene-2-carboxylic acid disodium salt A solution of 220 mL (0.227 mmol) of [6R-[6 alpha,7 beta (Z)]]-3-[[[3,4-bis(acetyloxy)benzoyl]oxy]methyl]-7-[[[(2-amino-4-thiazolyl)[1,1-dimethyl-2(1,1-dimethylethoxy)-2-oxoethoxy]imino]acetyl]amino]-8-oxo-5-thia-1-azabicyclo[4.2.0]oct-2-ene-2-carboxylic acid 1,1-dimethylethyl ester in 10 mL of CH$_2$Cl$_2$ and 1 mL of anisole was stirred at 0° C. while 10 mL TFA was added. Stirring was continued at 0° C. for 6 hours and the volatiles removed under reduced pressure. To the oily residue was added 5 mL of EtoAc, 5 mL of saturated NaHCO$_3$, and 5 mL of methanol and the two phase mixture stirred 30 minutes. The solution was concentrated under reduced pressure to a volume of about 5 mL, to which was added 5 mL of EtoAc and 5 mL of saturated sodium bicarbonate. The solution was stirred 15 minutes. The aqueous layer separated to yield 60 mg (33%) of a white solid after reverse phase chromatography (0–20% CH$_3$CN in H$_2$O).

NMR (DMSO-d$_6$): 1.40 (s) 3H (CMe$_2$); 1.49 (s) 3H (CMe$_2$); 3.31, 3.49 (d of d, J=16 Hz) 2H (CH$_2$S); 4.96, 5.04 (d of d, J=12 Hz) 2H (CH$_2$O); 5.05 (d J=6 Hz) 1H (C6); 5.68 (m) 1H (C7); 6.73 (m) 2H (Ar, thiazole); 7.18 (br) 2H (NH$_2$); 7.27 (d, J=8 Hz) 1H (Ar); 7.34 (s) 1H (Ar); 11.70 (d, J=10 Hz) 1H (NH). IR (KBr): 3350, 1762, 1670, 1598. MS: m/z 666 (M+H). UV (EtOH) λ max 218 nm (ε=25,050), λ max 262 nm (ε=17,600). HRMS Calc. (M+H) for C$_{24}$H$_{21}$N$_5$O$_{11}$S$_2$Na: 666.0553. Found: 666.0619.

EXAMPLE 21

Preparation of [6R-[6 alpha,7 beta(S)*)]]-3-[[[3,4-bis(acetyloxy)benzoyl]oxy]methyl]-7-[[[[(4-ethyl-2,3-dioxo-1-piperazinyl)carbonyl]amino]phenylacetyl]amino]-8-oxo-5-thia-1-azabicyclo[4.2.-0]oct-2-ene-2-carboxylic acid 1,1-dimethylethyl ester A suspension of 275 mg, (0.506 mmol) of (6R-trans)-7-amino-3-[[[3,4-bis(acetyloxy)benzoyl]oxy]methyl]-8-oxo-5-thia-1-azabicyclo[4.2.0]oct-2-ene-2-carboxylic acid 1,1-dimethylethyl ester monohydrochloride in 10 mL of CH$_2$Cl$_2$ was washed with 10 mL of a brine/saturated NaHCO$_3$ (4:1) mixture. The organic solution was separated and dried over MgSO$_4$. This solution was added to a solution of activated ester (prepared by adding 69 mg (0.506 mmol) of N-hydroxybenzotriazole followed by 104 mg (0.506 mmol) of 1,3-dicyclohexylcarbodiimide to a solution of 161 mg (0.506 mmol) of [[(4-ethyl-2,3-dioxo-1-piperazinyl)carbonyl]amino]-phenylacetic acid in 10 mL of dry THF and stirring 45 minutes.) The solution was stirred for 16 hours, filtered, and the solvent removed in vacuo. The residue was chromatographed (EtoAc) to give 250 mg (61%) of a cream colored solid.

NMR (CDCl$_3$): 1.20 (t, J=3 Hz) 3H (Et) 1.52 (s) 9H (t-bu); 2.32 (s) 6H (2OAc) 3.2–3.7 (m) 6H (CH$_2$S, Et, ½NCH$_2$CH$_2$N) 3.93 (m) 1H (½NCH$_2$CH$_2$N); 4.11 (m) 1H (½NCH$_2$CH$_2$N); 4.91 (d, J=6 Hz) 1H (C6); 5.00, 5.30 (d of d, J=14 Hz) 2H (CH$_2$O); 5.58 (d, J=8 Hz) 1H (NCHCPh); 5.84 (d of d, J=6 Hz, J=10 Hz) 1H (C7);

6.83 (d, J=10 Hz) 1H (NH); 7.20–7.35 (m) 6H (Ar); 7.80 (s) 1H (Ar); 7.89 (d, J=8 Hz) 1H (Ar); 10.04 (d, J=8 Hz) 1H (NH). IR (KBr): 3320, 1780, 1718, 1688. UV (EtOH): inf 225 nm ($\epsilon$=23,300), inf 270 nm ($\epsilon$=10,900).

EXAMPLE 22

Preparation of [6R-[6 alpha,7 beta(S)*)]]-3-[[[3,4-bis(acetyloxy)benzoyl]oxy]methyl]-7-[[[[(4-ethyl-2,3-dioxo-1-piperazinyl)carbonyl]amino]phenylacetyl]amino]-8-oxo-5-thia-1-azabicyclo[4.2.0]oct-2-ene-2-carboxylic acid monosodium salt By following the procedures and conditions described in Example 10, 100 mg (0.124 mmol) of [6R-[6 alpha,7 beta(S)*)]]-3-[[[3.4-bis(acetyloxy)benzoyl]oxy]methyl]-7-[[[[(4-ethyl-2,3-dioxo-1-piperazinyl)carbonyl]amino]phenylacetyl]amino]-8-oxo-5-thia-1-azabicyclo[4.2.0]oct-2-ene-2-carboxylic acid 1,1-dimethylethyl ester (Example 21) in 5 mL of $CH_2Cl_2$ and 500 $\mu$L of anisole, treated with 5 mL of TFA, followed by stirring for 5 hours, gave 48 mg (50%) of a white solid after reverse phase chromatography (0–30% $CH_3CN$ in $H_2O$).

NMR (DMSO-$d_6$): 1.08 (t, J=8 Hz) 3H (NEt); 2.31 (s) 6H (2OAc); 3.21–3.60 (m) 6H ($CH_2S$, NEt, ½$NCH_2CH_2N$) 3.91 (m) 2H (½$NCH_2CH_2N$); 4.92 (d, J=6 Hz) 1H (C6); 4.95, 5.25 (d, J=12 Hz) 2H ($CH_2O$); 5.57 (m) 1H (C7); 5.75 (d, J=8 Hz) 1H (NCHCPh); 7.26–7.48 (m) 6H (Ar); 7.82 (s) 1H (Ar); 7.89 (d, J=8 Hz) 1H (Ar); 9.41 (d, J=8 Hz) 1H (NH) 9.86 (d, J=10 Hz) 1H (NH). IR (KBr): 3420, 3305, 1772, 1715, 1682, 1610. UV (EtOH): $\lambda$ max 230 nm ($\epsilon$=22,600). HRMS calc. (M+H) for $C_{34}H_{33}NaN_5O_{13}S$: 774.1693. Found: 774.1729.

EXAMPLE 23

Preparation of [6R-[6 alpha,7 beta(S)*)]]-7-[[[[(4-ethyl-2,3-dioxo-1-piperazinyl)carbonyl]amino]phenylacetyl]amino]-3-[[(3,4-dihydroxy)benzoyl]oxy]methyl]-8-oxo-5-thia-1-azabicyclo[4.2.0]oct-2-ene-2-carboxylic acid monosodium salt By following the procedures and conditions described in Example 20, 150 mg (0.186 mmol) of [6R-[6 alpha,7 beta(S)*)]]-3-[[[3,4-bis(acetyloxy)benzoyl]oxy]methyl]-7-[[[[(4-ethyl-2,3-dioxo-1-piperazinyl)carbonyl]amino]phenylacetyl]amino]-8-oxo-5-thia-1-azabicyclo[4.2.0]oct-2-ene-2-carboxylic acid 1,1-dimethylethyl ester (Example 21) in 5 mL of $CH_2Cl_2$ and 500 $\mu$L of anisole, treated with 5 mL of TFA, followed by stirring with mixture of EtoAc, saturated $NaHCO_3$, MeOH(1:1:1), gave 68 mg (53%) of a white solid after reverse phase chromatography (0–20% $CH_3CN$ in $H_2O$).

NMR (DMSO-$d_6$): 1.01 (t, J=8 Hz) 3H (NEt); 3.14, 3.39 (d of d, J=18 Hz) 2H ($CH_2S$); 3.30–3.60 (m) 4H (NEt, ½$NCH_2CH_2N$); 3.85 (m) 2H (½$NCH_2CH_2N$); 4.80, 5.08 (d of d, J=12 Hz) 2H ($CH_2O$); 4.83 (d, J=6 Hz) 1H (C6); 5.48 (m) 1H (C7); 5.61 (d, J=8 Hz) 1H (NCHCPh); 6.69 (d, J=8 Hz) 1H (Ar); 7.16–7.41 (m) 7H (Ar); 9.33 (br) 1H (NH); 9.78 (d, J=8 Hz) 1H (NH). IR (KBr): 3400, 3300, 1762, 1712, 1680, 1603. MS: m/z 690 (M+H). UV (EtOH): $\lambda$ max 263 nm ($\epsilon$=17,900). HRMS calc. (M+H) for $C_{30}H_{29}N_5O_{11}SNa$: 690.1482. Found: 690.1517.

EXAMPLE 24

Preparation of [6R-[6 alpha,7 beta(Z)]]-3-[[[3,4-bis(acetyloxy)benzoyl]oxy]methyl]-7-[[[2-amino-4-thiazolyl][(2-amino-2-oxoethoxy)imino]acetyl]amino]-8-oxo-5-thia-1-azabicyclo[4.2.0]oct-2-ene-2-carboxylic acid monosodium salt By following the procedures and conditions described in Example 10, 200 mg (0.272 mmol) of [6R-[6 alpha,7 beta(Z)]]-3-[[[3,4-bis(acetyloxy)benzoyl]oxy]methyl]-7-[[[2-amino-4-thiazolyl][(2-amino-2-oxoethoxy)imino]acetyl]amino]-8-oxo-5-thia-1-azabicyclo[4.2.0]oct-2-ene-2-carboxylic acid 1,1-dimethylethyl ester (Example 18) in 4 mL of $CH_2Cl_2$ and 400 $\mu$L of anisole, treated with 4 mL of TFA, followed by stirring for 6 hours, gave 40 mg (21%) of a white solid after reverse phase chromatography (0–30% $CH_3CN$ in $H_2O$).

NMR (DMSO-$d_6$): 2.28 (s) 3H (OAc); 2.29 (s) 3H (OAc); 3.57 (d, J=18 Hz) 1H (½$CH_2S$, ½$CH_2S$ obscured by HOD); 3.99 (s) 2H ($CH_2ON$); 4.94 5.27 (d of d, J=12H) 2H ($CH_2OCO$); 5.01 (d, J=6 Hz) 1H (C6); 5.60 (d of d, J=6 Hz J=10 Hz) 1H (C7); 6.84 (s) 1H (thiazole); 7.10 (s) 2H ($NH_2$); 7.28 2H ($NH_2$); 7.41 (d, J=8 Hz) 1H (Ar); 7.84 (s) 1H (Ar); 7.89 (d, J=8 Hz) 1H (Ar). IR (KBr): 3440, 1768, 1710, 1710, 1678, 1610. MS: m/z 699 (M+H). UV ($H_2O$): $\lambda$ max 234 nm ($\epsilon$=26,260). HRMS calc. (M+H) for $C_{26}H_{26}NaN_6O_{12}S_2$: 699.0791. Found: 699.0822.

EXAMPLE 25

Preparation of (6R-cis)-3-[[(aminocarbonyl)oxy]methyl]-7-methoxy-8-oxo-7-(2-thienylacetyl)-amino-5-thia-1-azabicyclo[4.2.0]oct-2-ene-2-carboxylic acid (4-nitrophenyl)methyl ester To 3.75 g (8.30 mmol) of p-nitrobenzyl bromide in 100 mL dry DMF was added 3.75 g (8.30 mmol) of (6R-cis)-3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid sodium salt. The mixture was stirred for 2 hours, 30 minutes and 100 mL of ethyl acetate were added. The solution was washed with brine, dried with $MgSO_4$, and the solvent was removed in vacuo. The residue was chromatographed on silica gel using ethyl acetate/hexane as the elutant (1:1, then 2:1). The material obtained was crystallized from ethyl acetate/hexane to give 3.4 g (72%).

NMR ($CDCl_3$): 3.31, 3.49 (d of d, J=18 Hz) 2H ($CH_2S$); 3.44 (s) 3H ($OCH_3$); 3.79 (s) 2H ($CH_2CON$); 4.67 (br) 2H ($NH_2$); 4.82, 5.12 (d of d, J=14 Hz) 2H ($CH_2O$); 5.03 (s) 1H (C6); 5.31, 5.60 (d of d, J=14 Hz) 2H ($CH_2Ar$); 6.44 (s) 1H (NH); 6.99 (m) 2H (thiophene); 7.25 (m) 1H (thiophene); 7.56 (d, J=8 Hz) 2H (Ar); 8.19 (d, J=8 Hz) 2H (Ar). IR (KBr): 3465, 3335, 1785, 1728, 1698, 1522, 1348.

EXAMPLE 26

Preparation of (6R)-3-(iodomethyl)-7-methoxy-8-oxo-7-[(2-thienylacetyl)amino]-5-thia-1-azabicyclo[4.2.0]oct-2-ene-2-carboxylic acid (4-nitrophenyl)methyl ester To 3.0 g (5.33 mmol) of (6R-cis)-3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid (4-nitrophenyl)methyl ester (Example 25) in 75 mL of $CH_2Cl_2$ at ambient temperature was added 1.40 mL (10.3 mmol) of trimethylsilyl iodide. The mixture was stirred for 30 minutes and then washed with aqueous $NaHCO_3$ and dried with $MgSO_4$. The solvent was removed in vacuo and the residue chromatographed on silica gel (EtoAc/Hex 2:3) to give 2.88 g (86%) of a light yellow solid.

NMR ($CDCl_3$): 3.45, 3.60 (d of d, J=16 Hz) 2H ($CH_2S$); 3.49 (s) 3H ($OCH_3$); 3.94 (s) 2H ($CH_2CON$); 4.36, 4.50 (d of d, J=8 Hz) 2H ($CH_2I$); 5.07 (s) 1H (C6); 5.36, 5.46 (d of d, J=16 Hz) 2H ($CH_2Ar$); 6.46 (s) 1H (NH); 7.05 (m) 2H (thiophene); 7.30 (m) 1H (thiophene); 7.65 (d, J=8 Hz) 2H (Ar); 8.27 (d, J=8 Hz) 2H (Ar).

EXAMPLE 27

Preparation of
(6R-cis)-3-[[[3,4-bis(acetyloxy)benzoyl]oxy]methyl]-7-methoxy-8-oxo-7-[(2-thienylacetyl)amino]-5-thia-1-azabicyclo[4.2.0]oct-2-ene-2-carboxylic acid (4-nitrophenyl)methyl ester To 1.90 g (3.02 mmol) of (6R-cis)-3-(iodomethyl)-7-methoxy-8-oxo-7-[(2-thienylacetyl)amino]-5-thia-1-azabicyclo[4.2.0]oct-2-ene-2-carboxylic acid (4-nitrophenyl)methyl ester (Example 26) in 15 mL of dry DMF at 0° C. was added 0.78 g (3.00 mmol) of sodium 3,4-diacetoxybenzoate in one portion. The solution was stirred for 30 minutes and 100 mL EtOAc added. The resulting solution was washed with brine (3×50 mL), dried over $MgSO_4$, and the solvent removed in vacuo. Chromatography (hexane/EtoAc, 1:1) gave 1.30 g (58%) of a mixture of Δ2 and Δ3 isomers. This material was dissolved in 30 mL of $CH_2Cl_2$ at 0° C. and 400 mg (2.32 mmol) of m-chloroperbenzoic acid was added in one portion. The mixture was stirred at 0° C. for 2 hours, washed with aqueous $NaHCO_3$, dried over $MgSO_4$, and the solvent was removed in vacuo. Crystallization from EtoAc-hexane (5:2) gave 870 mg (66%) of a single sulfoxide isomer. The mother liquor was chromatographed on silica gel (EtoAc/$CH_2Cl_2$, 1:1) to give 320 mg (24%) of the isomeric sulfoxide. The combined sulfoxides (1.19 g 90%) were reduced by dissolving them in 5 mL of dry DMF at −20° C. and adding 0.34 mL of $PBr_3$, followed by stirring for 1 hour. Removal of the solvent in vacuo followed by silica gel chromatography (EtoAc/hexane 1:1) gave 967 mg (83%) of the title compound.

NMR ($CDCl_3$): 2.29 (s) 6H (2OAc); 3.33, 3.54 (d of d, J=18 Hz) 2H ($CH_2S$) 3.44 (s) 3H ($OCH_3$); 3.88 (s) ($CH_2CON$); 4.98 (d, J=12 Hz) 1H (½$CH_2O$); 5.04 (s) 1H (C6); 5.34 (m) 3H (½$CH_2O$, $CH_2$); 6.40 (s) 1H (NH); 6.99 (m) 2H (thiophene); 7.24 (m) 2H (thiophene, Ar); 7.54 (d, J=8H) 1H (Ar); 7.78 (s) 1H (Ar); 8.87 (d, J=8 Hz) 1H (Ar); 8.16 (d, J=8 Hz) 1H (Ar). IR (KBr): 3325, 1775, 1722, 1700, 1520, 1348. MS: m/z 740 (M+H).

EXAMPLE 28

Preparation of
(6R-cis)-3-[[[3,4-bis(acetyloxy)benzoyl]oxy]-methyl]-7-methoxy-8-oxo-7-[(2-thienylacetyl)amino]-5-thia-1-azabicyclo[4.2.0]oct-2-ene-2-carboxylic acid monosodium salt To a solution of 100 mg (0.135 mmol) of (6R-cis)-3-[[[3,4-bis(acetyloxy)benzoyl]oxy]methyl]-7-methoxy-8-oxo-7-[(2-thienylacetyl)amino]-5-thia-1-azabicyclo[4.2.0]oct-2-ene-2-carboxylic acid (4-nitrophenyl)methyl ester in 5 mL of THF was added 100 mg of 5% Pt/C. The mixture was hydrogenated at 50 psi for 48 hours. The mixture was filtered to remove the catalyst and the solvent was removed in vacuo. The residue was taken up in 3 mL of EtoAc and 3 mL of 2% aqueous $NaHCO_3$ and stirred vigorously for 15 minutes. The aqueous layer was separated and chromatographed (reverse phase, 0–30% $CH_3CN$ in $H_2O$) to give 45 mg (53%) of a white solid after lyophilization of the appropriate fractions.

NMR (DMSO-$d_6$): 2.32 (s) 6H (20 Ac); 3.19, 3.59 (d of d, J=18 Hz) 2H ($CH_2S$); 3.49 (s) 3H ($OCH_3$); 3.79, 3.89 (d of d, J=16 Hz) 2H ($CH_2CO$); 4.98, 5.17 (d of d, J=14 Hz) 2H ($CH_2O$); 5.00 (s) 1H (C6); 6.96 (m) 2H (thiophene); 7.38 (m) 1H (thiophene); 7.45 (d, J=8 Hz) 1H (Ar); 8.84 (s) 1H (Ar); 8.91 (d, J=8 Hz) 1H (Ar); 9.41 (s) 1H NH. IR (KBr): 3400, 1770, 1618, 1612. MS: m/z 672 (M+H). UV (EtOH): λ max 236 nm (ε=16,620). HRMS calc. (M+H) for $C_{26}H_{24}NaN_2O_{11}S_2$: 627.0719. Found: 627.0676.

EXAMPLE 29

Preparation of
(6R-cis)-3-[[(3,4-dihydroxybenzoyl)oxy]methyl]-7-methoxy-8-oxo-7-[(2-thienylacetyl)amino]-5-thia-1-azabicyclo[4.2.0]oct-2-ene-2-carboxylic acid monosodium salt To a solution of 65 mg (0.104 mmol) of (6R-cis)-3-[[[3,4-bis(acetyloxy)benzoyl]oxy]methyl]-7-methoxy-8-oxo-7-[(2-thienylacetyl)amino]-5-thia-1-azabicyclo[4.2.0]oct-2-ene-2-carboxylic acid sodium salt (Example 28) in 4 mL of saturated aqueous $NaHCO_3$ was added 1 mL of methanol. The solution was stirred at ambient temperature for 1 hour. The methanol was removed under reduced pressure and the remaining aqueous solution chromatographed (reverse phase, 0–20% $CH_3CN$ in $H_2O$) to give 52 mg (92%) of white solid after lyophilization of the appropriate fractions.

NMR (DMSO-$d_6$): 3.11 (d of d, J=18 Hz) 1H (½ $CH_2S$, other ½ obscured by HOD); 3.37 (s) 3H ($OCH_3$); 3.78, 3.87 (d of d, J=16 Hz) 2H ($CH_2CO$); 4.83, 5.01 (d of d, J=12 Hz) 2H ($CH_2O$); 4.98 (s) 1H (C6); 5.40 (br) 3H (2OH, NH); 6.38, 6.95 (m) 1H (Ar); (m) 2H (thiophene); 7.11 (s) 1H (Ar); (d, J=8 Hz) 1H (Ar); 7.36 (m) 1H (thiophene). IR (KBr): 1762, 1675, 1610. MS: m/z 543 (M+H). UV (EtOH): λ max 222 nm (ε=15,960), λ max 265 nm (ε=10,280). HRMS calc. (M+H) for $C_{22}H_{20}N_2O_9S_2Na$: 543.0508. Found: 543.0506.

EXAMPLE 30

Preparation of [6R-[6 alpha,7 beta(Z)]]-3-[[[3,4-bis(acetyloxy)benzoyl]amino]methyl]-7-[[(2-amino-4-thiazolyl)(methoxyimino)acetyl]amino]-5-thia-1-azabicyclo[4.2.0]oct-2-ene-2-carboxylic acid monosodium salt To a solution of 61.3 mg (0.258 mmol) of 3,4-diacetoxybenzoic acid in 10 mL of dry DMF was added 68 mg (0.258 mmol) of triphenylphosphine followed by 86 mg of 2,2'-dibenzothiazolyl disulfide. Complete solution occurred within 20 minutes and the solution was stirred for 10 minutes thereafter. To this solution was added dropwise a solution of 100 mg (0.206 mmol) of [6R-[6 alpha,7 beta(Z)]]-3-(aminomethyl)-7-[[(2-amino-4-thiazolyl)(methoxyimino)acetyl]amino]-5-thia-1-azabicyclo[4.2.0]oct-2-ene-2-carboxylic acid monohydrochloride salt and 150 μl of triethylamine in 5 mL of dry DMF. The resulting solution was stirred for 3 hours and the solvent was removed in vacuo. To the residue was added 5 mL of ethyl acetate and 5 mL of 2% aqueous $NaHCO_3$. The two-phase mixture was stirred rapidly for 15 minutes and the aqueous portion separated and chromatographed (reverse phase, 0–30% CH$_3$CN in H$_2$O), giving 62 mg (45%) of a white solid.

NMR (DMSO-d$_6$): 2.30 (s) 6H (20 Ac); 3.21, 3.54 (d of d, J=18 Hz) 2H (CH$_2$S); 3.82 (s) 3H (OCH$_3$); 3.99 (d of d, J=12 Hz, J=4 Hz) 1H (½ CH$_2$N); 4.05 (d of d, J=12 Hz) 1H (½ CH$_2$N); 4.95 (d, J=6 Hz) 1H (C6); 5.52 (d of d, J=6 Hz, J=10 Hz) 1H (C7); 6.72 (s) 1H (thiazole); 7.20 (s) 2H (NH$_2$); 7.36 (d, J=8 Hz) 1H (Ar); 7.70 (s) 1H (Ar); 7.75 (d, J=8 Hz) 1H (Ar); 9.20 (br) 1H (NH), 9.49 (d, J=10 Hz) 1H (NH). IR (KBr): 3360, 1763, 1645, 1612. M.S.: m/z 655 (M+H). UV (EtOH): λ max 228 nm (ε=21,250). HRMS calc. (M+H) for C$_{25}$H$_{25}$NaN$_6$O$_{10}$S$_2$: 655.0893. Found 655.0886

EXAMPLE 31

Preparation of [6R-[6 alpha,7 beta(Z)]]-3-[[[(3,4-dihydroxy)benzoyl]amino]methyl]-7-[[(2-amino-4-thiazolyl)(methoxyimino)acetyl]amino]-5-thia-1-azabicyclo[4.2.0]oct-2-ene-2-carboxylic acid monosodium salt By following the procedures and conditions described in Example 29, 20 mg (0.031 mmol) of [6R-[6 alpha,7 beta(Z)]]-3-[[[(3,4-bis(acetyloxy)benzoyl]amino]methyl]-7-[[2-amino-4-thiazolyl]-(methoxyimino)acetyl]amino]-5-thia-1-azabicyclo[4.2.0]oct-2-ene-2-carboxylic acid monosodium salt (Example 30) in 1 mL of saturated aqueous NaHCO$_3$ and 500 μL of methanol gave 10 mg (60%) of a white solid after chromatography (reverse phase, 0–20% CH$_3$CN) and lyophilization.

NMR (D$_2$O): 3.38, 3.67 (d of d, J=18 Hz) 2H (CH$_2$S); 3.99 (s) 3H (OCH$_3$); 4.13, 4.39 (d of d, J=14 Hz) 2H (CH$_2$N); 5.21 (d, J=6 Hz) 1H (C6); 5.30 (d, J=6 Hz) 1H (C7); 6.75 (d, J=8 Hz) 1H (Ar); 7.02 (s) 1H (thiazole); 7.22 (m) 2H (Ar). HRMS calc. (M+H) for C$_{21}$H$_{19}$NaN$_6$O$_8$S$_2$: 571.0862. Found: 571.0646.

EXAMPLE 32

Preparation of [6R-[6 alpha,7 beta(Z)]]-7-[[(2-amino-4-thiazolyl)(methoxyimino)acetyl]amino]-3-[[(3,4-dihydroxybenzoyl)thio]methyl]-8-oxo-5-thia-azabicyclo[4.2.0]oct-2-ene-2-carboxylic acid monosodium salt To a suspension of 2.03 g (8.0 mmol) of 3,4-bis (acetyloxy)benzenecarbothioic acid in 80 mL H$_2$O was added 2.02 g (24.0 mmol) of NaHCO$_3$. The resulting solution was stirred at 50° for 15 minutes. To this was added a solution of 3.82 g (8.0 mmol) of 3-[(acetyloxy)methyl]-7-[[(2-amino-4-thiazolyl)(methoxyimino)acetyl]amino]-8-oxo-5-thia-1-azabicyclo[4.2.0]oct-2-ene-2-carboxylic acid monosodium salt in 20 mL of H$_2$O. The reaction was stirred at 50° C. for 18 hours, cooled, filtered and chromatographed (C$_{18}$, 0–20% CH$_3$CN in H$_2$O) to give 1.55 g (29%) after lyophilization.

NMR (D$_2$O): 3.35, 3.75 (d of d, J=18 Hz) 2H (CH$_2$S); 3.86, 4.23 (d of d, J=14 Hz) 2H (CH$_2$SCO); 3.98 (s) 3H (OCH$_3$); 5.19 (d, J=6 Hz) 1H (C6); 5.79 (d, J=6H) 1H (C7); 6.96 (d, J=8 Hz) 1H (Ar); 7.01 (s) 1H (thiazole); 7.45 (s) 1H (Ar); 7.52 (d, J=8 Hz). IR (KBr); 3345, 1770, 1695, 1600. UV (H$_2$O): λ max 203 nm (λ=36,500), λ max 230 nm (ε=32,000), λ max 250 nm (ε=24,000). HRMS calc (M+H) for C$_{21}$H$_{19}$ NaN$_5$O$_8$S$_3$: 588.0294. Found: 588.0287.

EXAMPLE 33

Preparation of [6R-[6 alpha,7 beta(Z)]]-3[[(3,4-bis(acetyloxy)benzoyl)thio]methyl]-8-oxo-7-[[[2-[(triphenylmethyl)amino]-4-thiazoyl](methoxy-imino)acetyl]amino]-5-thia-1-azabicyclo[4.2.-0]oct-2-ene-2-carboxylic acid 1,1-dimethylethyl ester By following the procedures and conditions described in Example 4, 61 mg (0.220 mmol) of 3,4-bis-(acetyloxy) benezenecarbothioic acid monosodium salt in 2 ml of dry DMF was added to 171 mg (0.208 mmol) of [6R-[6 alpha,7 beta(Z)]]-3-(iodomethyl)-7-[[2-(methoxyimino)-2-[2-(tritylamino)-4-thiazolyl]-acetyl-amino]-8-oxo-5-thia-1-azabicyclo[4.2.0]oct-2-ene-2-carboxylic acid 1,1-dimethylethyl ester in 2 ml of DMF, followed by stirring for 3 hours, gave 112 mg (57%) of a cream colored solid after silica gel chromatography (9:1 CH$_2$Cl$_2$/MeOH).

NMR (CDCl$_3$): 1.54 (s) 9H (t-Bu); 2.31 (s) 6H (2 OAc); 2.32, 2.62 (d of d, J=18 Hz) 2H (CH$_2$S); 4.05, 4.30 (d of d, J=10 Hz) 2H (CH$_2$SCO); 5.02 (d, J=6 Hz) 1H (C6); 5.90 (d of d, J=6 Hz, J=10 Hz) 1H (C7) 6.68 (d, J=10 Hz) 1H (NH) 6.70 (s) 1H (thiazole); 6.99 (br s) 1H (NH) 7.26 (s) 16H (CPh$_3$, Ar); 7.81 (s) 1H (Ar); 7.86 (d, J=8 Hz) 1H (Ar). I.R. (KBr): 1780, 1715, 1665. U.V. (EtOH): λ max 214 nm(ε=36,000), λ max 267 nm(ε=29,750). M.S.: M/Z 948 (M+H).

EXAMPLE 34

Preparation of [6R-[6 alpha,7 beta(Z)]]-7-[[(2-amino-4-thiazolyl)(methoxyimino)acetyl]amino]-3-[[[(3,4-bis(acetyloxy)benzoyl]thio]methyl]-8-oxo-5-thia-1-azabicyclo[4.2.0]-oct-2-ene-2-carboxylic acid monosodium salt By following the procedures and conditions described in Example 10, 208 mg (0.219 mmol) of [6R-[6 alpha,7 beta(Z)]]-3[[(3,4-bis(acetyloxy)benzoyl)thio]methyl]-8-oxo-7-[[[2-[(triphenylmethyl)amino]-4-thiazolyl](methoxyimino)acetyl]amino]-5-thia-1-azabicyclo[4.2.0]oct-2-ene-2-carboxylic acid 1,1-dimethylethyl ester (Example 33) in 4 mL of CH$_2$Cl$_2$ and 500 μL of anisole, treated with 4 mL of TFA, followed by stirring for 5 hours, gave 77 mg (52%) of white powder after reverse phase chromatography (0–20% CH$_3$CN in H$_2$O)

NMR (D$_2$O): 2.40 (s) 6H (2OAc); 3.39, 3.73 (d of d, J=18 Hz) 2H (CH$_2$S); 4.01 (s) 3H (OCH$_3$); 3.96, 4.39 (d of d, J=14 Hz) 2H (CH$_2$SCO); 5.21 (d, J=6 Hz) 1H (C6); 5.81 (d, J=6 Hz) 1H (C7); 7.03 (s) 1H (thiazole) 7.45 (d, J=8 Hz) 1H (Ar); 7.89 (s) 1H (Ar); 8.98 (s) 1H (Ar). U.V. (H$_2$O): λ max 237 nm (ε=20,200), λ max 275 nm (ε=17,000). M.S.: M/Z 672 (M+H).

EXAMPLE 35

Preparation of [6R-[6 alpha,7 beta(Z)]]-3-[[(3,4-bis(acetyloxy)-2,5-dichloro)oxy]methyl]-7-[[(methoxyimino)[2-[(triphenylmethyl)amino]-4-thiazolyl]acetyl]amino]-8-oxo-5-thia-1-azabicyclo-[4.2.0]oct-2-ene-2-carboxylic acid 1,1-dimethylethyl ester By following the procedures and conditions described in Example 4, 87 mg (0.264 mmol) of 3,4-bis-(acetyloxy)-2,5-dichlorobenzoic acid sodium salt in 2 ml of DMF added to 208 mg (0.253 mmol) of [6R-[6 alpha,7 beta(Z)]]-3-(iodomethyl)-7-[[2-(methoxyimino)-2-[2-(tritylamino)-4-thiazolyl]-acetyl]amino]-8-oxo-5-thia- 1-azabicyclo[4.2.0]oct-2-ene-2-carboxylic acid 1,1-dimethylethyl ester in 2 ml of DMF, followed by stirring for 4 hours gave 176 mg (70%) after silica gel chromatography (9:1 $CH_2Cl_2$/MeOH).

NMR ($CDCl_3$): 1.50 (s) 9H (tBu); 2.36 (s) 6H (2 OAc); 2.36, 2.60 (d of d J=18 Hz) 2H ($CH_2S$); 4.03 (s) 3H ($OCH_3$) 5.01 (m) 2H (½ $CH_2O$, C6) 5.38 (d, J=14 Hz) 1H (½ $CH_2O$) 5.92 (d of d, J=6 Hz, J=10 Hz) 1H (C7); 6.68 (m) 2H (NH, thiazole) 7.12 (s) 15H ($CPh_3$); 7.81 (s) 1H (Ar).

EXAMPLE 36

Preparation of [6R-[6 alpha,7 beta(Z)]]-7-[[(2-amino-4-thiazolyl)(methoxyimino)acetyl]amino]-3-[[(3,4-bis-(acetyloxy)-2,5-dichlorobenzoyl)oxy]methyl]-8-oxo-5-thia-1-azabicyclo[4.2.0]oct-2-ene-2-carboxylic acid monosodium salt A solution of 146 mg (0.146 mmol) of [6R-[6 alpha,7 beta(Z)]]-3-[[[3,4-bis(acetyloxy)-2,5-dichloro]oxy]methyl]-7-[[(methoxyimino)[2-[(triphenylmethyl)amino]-4-thiazolyl]amino]-8-oxo-5-thia-1-azabicyclo[4.2.0]oct-2-ene-2-carboxylic acid 1,1-dimethylethyl ester in 4.6 mL of 70% aqueous formic acid was stirred for 3 hours at ambient temperature. The solvent was removed in vacuo and the residue chromatographed on silica gel (0–100% EtOAc in $CH_2Cl_2$) to give 80.7 mg (72%) of detritylated material. A solution of 39 mg (0.051 mmol) of this material in 1.4 ml of $CH_2Cl_2$ and 100 μL of anisole was cooled to 0° and treated with 1.2 mL of TFA. The reaction was stirred for 6½ hours at 0° C. and the solvent removed in vacuo. The oily residue was dissolved in 1 ml of acetone and added to 50 ml hexanes with stirring. The resulting precipitate was filtered and dissolved in 0.5 ml of EtOAc and treated with 9.0 mg (0.054 mmol) of 2-ethyl sodium hexanoate. The precipitate was collected and dried to give 7 mg (19%) of a white solid. NMR ($D_2O$). 2.30 (s) 6H (2 OAc); 3.30, 3.60 (d of d, J=18 Hz) 2H ($CH_2S$); 3.82 (s) 3H ($OCH_3$) 4.80 (d, J=12 Hz) 1H (½ $CH_2O$); 5.06 (m) 2H (½ $CH_2O$, C6); 5.66 (d, J=6 Hz) 1H (C7); 6.84 (s) 1H (thiazole); 7.91 (s) 1H (Ar).

EXAMPLE 37

Preparation of [(6R-trans)-3-[[[[[3,4-bis(acetyloxy)phenyl]amino]carbonyl]oxy]methyl]-7-[[(1,1-dimethylethoxy)-carbonyl]amino]-8-oxo-5-thia-1-azabicyclo[4.2.0]oct-2-ene-2-carboxylic acid diphenylmethyl ester To a solution of 160 mg (0.8 mmol) of 3,4-bis-(acetyloxy)phenylisocyanate in 7 ml of dry methylene chloride was added 0.2 ml of pyridine, followed by the addition of 198 mg (0.4 mmol) of (6R-trans)-3-[hydroxymethyl]-7-[[(1,1-dimethylethoxy)carbonyl]amino]-8-oxo-5-thia-1-azabicyclo[4.2.0]oct-2-ene-2-carboxylic acid diphenylmethyl ester under argon at ambient temperature. The reaction was stirred for 5 hours and the solvent removed in vacuo. The residue was taken up in EtOAc and the organic solution was washed with dilute HCl, dried over anhydrous $Na_2SO_4$. The crude product was purified on silica chromatograph (EtOAc/hexane, 1:1) to give 250 mg (84%) of a white solid.

NMR ($CDCl_3$): 1.46 (s) 9H (t-bu); 2.28 (s) 6H (2-OAc); 3.43, 3.64 (d of d, J=18 Hz) 2H ($CH_2S$); 4.84, 5.18 (d of d, J=12 Hz) 2H ($CH_2O$); 4.95 (d, J=6 Hz) 1H (C6); 5.68 (d of d, J=6 Hz J=10 Hz) 1H (C7); 5.23 (d, J=10H) 1H (NH); 6.62 (s), 1H (thiazole, Ar); 7.0 (s) 1H (CH Ar2); 7.14 (s) 2H (Ar); 7.36 (m) 1H (Ar). IR (KBr): 3340, 1773, 1722, 1530, 700.

EXAMPLE 38

Preparation of [6R-[6 alpha,7 beta(Z)]]-3[[[[3,4-bis(acetyloxy)phenyl]amino]carbonyl]oxymethyl]-7-[[(2-amino-4-thiazolyl)(methoxyimino)acetyl]amino]-8-oxo-5-thia-1-azabicyclo[4.2.0]oct-2-ene-2-carboxylic acid monosodium salt A solution of 233 mg (0.31 mmol) of [(6R-trans)-3-[[[[[3,4-bis(acetyloxy)phenyl]amino]carbonyl]oxy]methyl]-7-[[(1,1-dimethylethoxy)carbonyl]amino]-8-oxo-5-thia-1-azabicyclo[4.2.0]oct-2-ene-2-carboxylic acid diphenylmethyl ester from Example 37 in 5 ml of dry 1,2-dichloroethane was cooled to 0° C. in a ice/water bath and treated with 0.6 ml of anisole followed by 4 mL of trifluoroacetic acid. The reaction was stirred at 0° C. for 5 hours, and the volatiles were removed in vacuo. The residue was precipitated with anhydrous diethyl ether and filtered. The solid (130 mg) in 10 ml of dry methylene chloride and 0.1 ml of triethylamine at 0° C. was added to 106 mg (0.33 mmol) of s-(2-benzothiazoyl)-(Z)-amino-thio-4-thiazole-glyoxylate-o-(methyl)-oxime and 5 ml of acetone. The mixture was stirred under argon at ambient temperature for 15 hours. Solvents were removed in vacuo and the residue was added to 5 ml of EtOAc and 10 ml 1% aqueous $NaHCO_3$ solution. The aqueous solution was purified on $C_{18}$ reverse phase chromatograph (0–20% $CH_3CN$ in $H_2O$) to give 39 mg (20%) of desired product.

NMR (DMSO-$d_6$): 2.23 (s) 3H (OAc); 2.26 (s) 3H (OAc); 3.24, 3.50 (d of d, J=18 Hz) 2H ($CH_2S$); 3.84 (s) 3H ($OCH_3$); 4.90, 4.98 (d of d, J=12 Hz) 2H ($OCH_2$); 5.0 (d, J=6 Hz) 1H (C6); 5.60 (d of d, J=6 Hz J=10 Hz) 1H (C7); 6.78 (s) 1H (thiazole); 7.18 (d, J=8 Hz) 1H (Ar); 7.32 (d of d J=3 Hz J=8 Hz) 1H (Ar) 7.44 (d, J=3 Hz) 1H (Ar); 7.30 (br s) 2H ($NH_2$); 9.56 (br d, J=10 Hz), 1H (NH). Ir (KBr): 3330, 1762, 1672, 1732 inf. 1612.

EXAMPLE 39

Preparation of [6R-[6 alpha,7 beta(Z)[[-3-[[[[3,4-bis(acetyloxy)phenyl]amino]carbonyl]oxymethyl]-7-[[[2-amino[2-amino-2-oxoethoxy]imino]-4-thiazolyl]acetyl]amino]-8-oxo-5-thia-1-azabicyclo[4.2.0]oct-2-ene-2-carboxylic acid monosodium salt By following the procedures and conditions described in Example 38, 233 mg (0.31 mmol) of [(6R-trans)-3-[[[[3,4-bis(acetyloxy)phenyl]amino]carbonyl]oxy]methyl]-7-[[(1,1-dimethylethoxy)carbonyl]amino]-8-oxo-5-thia-1-azabicyclo[4.2.0]oct-2-ene-2-carboxylic acid diphenylmethyl ester in 5 ml of dry 1,2-dichloroethane and 0.6 ml of anisole was treated with 4 ml of trifluoroacetic acid, followed by reaction with 87 mg (0.22 mmol) of s-(2-benzothiazolyl)-Z-aminothio-4-thiazole-glyoxylate O-(carbamoylmethyl)oxime. Purification on $C_{18}$ reverse phase chromatography (0–20% $CH_3CN$ in $H_2O$) gave 48 mg (23%) of a white solid.

NMR (DMSO-$d_6$): 2.23 (s) 3H (OAc); 2.26 (s) 3H (OAc); 3.24, 3.52 (d of d, J=16 Hz) 2H ($CH_2S$); 4.42 (s) 2H ($CH_2CON$); 4.93 (s) 2H ($OCH_2$); 5.03 (d, J=6 Hz) 1H (C6); 5.64 (d of d, J=6 Hz J=10 Hz) 1H (C7); 6.87 (s) 1H (thiazole); 7.17 (d, J=9 Hz) 1H (Ar); 7.32 (d of d, J=3 Hz J=9 Hz) 1H (Ar); 7.35 (br s) 2H ($NH_2$); 7.42 (d, J=3 Hz) 1H (Ar); 9.75 (d, J=10 Hz) 1H (NH); 10.15 (br s) 1H (NH).

EXAMPLE 40

Preparation of
[(6R-trans)-3-[[[(3,4-bis(acetyloxy)benzoyl]-thio]methyl]-8-oxy-7-[(phenoxyacetyl)amino]-5-thia-1-azabicyclo[4.2.0]oct-2-ene-2-carboxylic acid 1,1-dimethylethyl ester By following the procedures and conditions described in Example 4, 230 mg (0.832 mmol) of 3,4-bis-(acetyloxy)benzenecarbothioic acid sodium salt in a 5 ml of DMF added to 411 mg (0.775 mmol) of [6R-[6 alpha, 7 beta(Z)]]-3-iodomethyl-7-[(phenoxyacetyl)amino]-8-oxo-5-thia-1-azabicyclo[4.2.0]-oct-2-ene-2-carboxylic acid 1,1-dimethylethyl ester in 5 ml DMF, followed by stirring for 2.5 hours, gave 206 mg (40%) of a white solid after silica gel chromatography (9:1 $CH_2Cl_2$/EtOAc).

NMR ($CDCl_3$): 1.44 (s) 9H (t-Bu); 2.42 (s) 6H (2 OAc); 3.35, 3.61 (d of d, J=18 Hz) 2H ($CH_2S$); 4.00, 4.29 (d of d, J=12 Hz) 2H ($CH_2SCO$); 4.55 (s) 3H ($OCH_3$); 5.01 (d, J=6 Hz) 1H (C6) 5.91 (d of d, J=6 Hz, J=10 Hz) 1H (C7); 6.90 (d, J=8 Hz) 1H (Ar); 7.00 (m) 1H (Ar); 7.2, 7.3 (m) 3H (Ar); 7.79 (s) 1H (Ar); 7.86 (d, J=8 Hz) 1H (Ar). IR (KBR): 3320, 1780, 1712, 1692, 1662. UV (EtOH): λ max 248 nm (ε=17,000), λ max 274 nm (ε=1,850).

EXAMPLE 41

Preparation of
(6R-trans)-7-amino-3-[[[3,4-bis-(acetyloxy)benzoyl]thio]methyl]-8-oxo-5-thia-1-azabicyclo[4.2.0]oct-2-ene-2-carboxylic acid 1,1-dimethylethyl ester monohydrochloride By following the procedures and conditions described in Example 16, 147 mg (0.223 mmol) of (6R-trans)-3-[[[(3,4-bis-(acetyloxy)benzoyl]thio]methyl]-8-oxo-7-[(phenoxyacetyl)amino]-5-thia-1-azabicyclo[4.2.-0]oct-2-ene-2-carboxylic acid 1,1-dimethylethyl ester in 0.7 ml $CH_2Cl_2$ was added to 27 μl (0.333 mmol) of pyridine and 61.7 mg (0.296 mmol) of $PCl_5$ to give 70.5 mg (56%) of a white powder.

NMR (DMSO-$d_6$): 1.53 (s) 9H (t-Bu); 2.30 (s) 3H (OAc); 2.31 (s) 3H (OAc); 3.54, 3.83 (d of J, J=18 Hz) 2H ($CH_2S$); 3.96, 4.33 (d of d, J=12 Hz) 2H ($CH_2SCO$); 5.17 (d, J=6 Hz) 1H (C6); 5.22 d, J=6 Hz) 1H (C7); 7.48 (d, J=8 Hz) 1H (Ar); 7.84 (s) 1H (Ar); 7.88 (d, J=8 Hz) 1H (Ar). IR (KBr): 1780, 1712, 1668. UV (EtOH): λ max 277 nm (ε=16,760)

EXAMPLE 42

[6R-[6 alpha,7 beta(Z)[[-7-[[[2-amino[(2-amino-2-oxoethoxy)imino]-4-thiazolyl]acetyl]amino]-3-[[(3,4-dihydroxybenzoyl)oxy]-methyl]-8-oxo-5-thia-1-azabicyclo-[4.2.0]oct-2-ene-2-carboxylic acid monosodium salt By following the procedures and conditions described in Example 20, 350 mg (0.477 mmol) of [6R-[6 alpha,7 beta(Z)]]-3-[[[3,4-bis(acetyloxy)benzoyl]oxy]-methyl]-7-[[[2-amino](2-amino-2-oxoethoxy)imino]-4-thiazolyl]acetyl]amino]-8-oxo-5-thia1-azabicyclo[4.2.-0]oct-2-ene-2-carboxylic acid 1,1-dimethyl-ethyl ester in 5 mL of $CH_2Cl_2$ and 500 μL of anisole, treated with 5 ml of TFA, followed by stirring the residue with EtOAc, MeOH and saturated $NaHCO_3$ (1:1:1), gave 165 mg (54%) of a white solid after reverse phase chromatography (0-20% $CH_3CN$ in $H_2O$).

NMR (DMSO$d_6$): 3.56 (d, J=18 Hz) 1H (½ $CH_2S$); 4.41 (s) 2H ($CH_2$); 4.89 5.17 (d of d, J=12 Hz) 2H ($CH_2OCO$); 5.05 (d,J=6 Hz) 1H (C6); 5.64 (d of d, J=6 Hz, J=10 Hz) 1H (C7); 6.77 (d, J=8 Hz) 1H (Ar); 6.84 (s) 1H (thiazole); 7.12 (s) 1H (OH); 7.29 (d, J=8 Hz) 1H (Ar); 7.34 (s) 1H (Ar); 7.50 (s) 1H (OH) 9.75 (d, J=8 Hz) 1H (NH). I.R. (KBr): 1762 1672 1608. UV ($H_2O$): λ max 218 nm (ε=17,900), λ max 261 (ε=14,350). Exact mass calc. for $C_{22}H_{21}N_6O_{10}S_2Na$ (M+H): 616.0614. Found: 616.0658

EXAMPLE 43

[6R-[6 alpha, 7 beta(Z)]]-3-[[[3,4-bis(acetyloxy)benzoyl]thio]methyl]-7-[[[(2-amino-2-oxoethoxy)imino](2-amino-4-thiazolyl)-acetyl]amino]-8-oxo-5-thia-1-azabicyclo[4.2.0]oct-2-ene-2-carboxylic acid 1,1-dimethylethyl ester By following the procedures and conditions described in Example 18, 243 mg (0.434 mmol) of (6R-trans)-3-[[[3,4-bis(acetyloxy)benzoyl]thio]methyl]-7-amino-8-oxo-5-thia-1-azabicyclo[4.2.0]oct-2-ene-2-carboxylic acid 1,1-dimethylethyl ester monohydrochloride and 158 mg (0.400 mmol) of S-(2-benzothiazoyl)-Z-aminothio-4-thiazoyl-glyoxylate-O-(carbamoylmethyl) oxime in 8 ml of DMF and 16 ml of $CH_2Cl_2$ gave 180 mg of a white solid after chromatography (0-50% $CH_3OH$ in $CH_2Cl_2$)

NMR ($CDCl_3$): 1.57 (s) 9H (t-Bu); 2.31 (s) 6H (2 OAc); 3.39, 3.63 (d of d, J=18 Hz) 2H ($CH_2S$) 3.98, 4.36 (d of d, J=15 Hz) 2H ($CH_2SCO$); 5.07 (d, J=6 Hz) 1H (C6); 5.60 (br) 2H ($NH_2$); 5.95 (d of d, J=6 Hz, J=10 Hz) 1H (C7); 6.85 (s) 1H (thiazole); 7.30 (d, J=8 Hz) 1H (Ar); 7.80 (d, J=2 Hz) 1H (Ar); 7.88 (d of d, J=2 Hz, J=8 Hz) 1H (Ar); 8.32 (br) 1H (NH). IR (KBr): 1778, 1710, 1672. UV (EtOH): λ max 240 nm (ε=20,750), λ max 278 nm (ε=17,300). M.S.: M/Z 749 (M+H).

EXAMPLE 44

[6R-[6 alpha,7 beta(Z)]]-7-[[[2-amino[(2-amino-2-oxoethoxy]imino]-4-thiazolyl]acetyl]amino]-3-[[(3,4-dihydroxybenzoyl)thio]-methyl]-8-oxo-5-thia-1-azabicyclo[4.2.0]oct-2-ene-2-carboxylic acid monosodium salt By following the procedures and conditions described in Example 20, 305 mg (0.408 mmol) of [6R-[6 alpha,7 beta(Z)]]-3-[[[3,4-bis(acetyloxy)benzoyl]thio]-methyl]-7-[[[(2-amino-2-oxoethoxy)imino](2-amino-4-thiazolyl)acetyl]amino]-8-oxo-5-thia-1-azabicyclo[4.2.-0]oct-2-ene-2-carboxylic acid 1,1-dimethylethyl ester in 6 ml of $CH_2Cl_2$ and 600 μL of anisole, treated with 13 ml of TFA, followed by stirring the residue with EtOAc, MeOH and saturated $NaHCO_3$ (1:1:1), gave 200 mg of a white solid after reverse phase chromatography (0-20% $CH_3CN$ in $H_2O$). NMR (DMSO-$d_6$): 3.09, 3.51 (d of d, J=18 Hz) 2H ($CH_2S$); 4.03, 4.18 (d of d, J=12 Hz) 2H ($CH_2SCO$) 4.41 (s) 2H ($OCH_2$); 5.00 (d, J=6 Hz) 1H (C6); 5.59 (d of d J=6 Hz, J=10 Hz) 1H (C7); 6.79 (d, J=8 Hz) 1H (Ar); 6.83 (s) 1H (thiazole); 7.09 (s) 1H (OH); 7.30 (m) 6H (2Ar, 2$NH_2$) 7.48 (s) 1H (OH); 9.73 (d, J=10 Hz) 1H (NH). Ir (KBr): 1760, 1672, 1592, 1162, 1088. UV ($H_2O$): λmax 230 (ε=16850); λmax 282 (ε=12,900). HRMS calc or $C_{22}H_{19}N_6O_9S_3Na$: 631.0375: Found: 631.0352.

EXAMPLE 45

[6R-[6 alpha,7 beta (Z)]]-3-[[[3,4-bis(acetyloxy)benzoyl]oxymethyl]-7-[[(2-amino-4-thiazolyl)[[2-(1,1-dimethylethoxy)-2-oxoethyoxy]imino]acetyl]amino]-8-oxo-5-thia-1-azabicyclo[4.2.0]oct-2-ene-2-carboxylic acid 1,1-dimethylethyl ester By following the procedures and conditions described in Example 18, 1.20 g (2.37 mmol) of (6R-trans)-7-amino-3[[[3,4-bis(acetyloxy)benzoyl]oxy]methyl-8-oxo-5-thia-1-azabicyclo[4.2.0]oct-2-ene-2-carboxylic acid 1,1-dimethylethyl ester monohydrochloride in 46 ml $CH_2Cl_2$ and 1.0 g (222 mmol) of 2-[[[1-(2-amino-4-thiazoyl)-2-(benzothiazol-2-yl-thio)-2-oxoethyl]imino]acetic acid 1,1-dimethylethyl ester in 46 ml of DMF and 23 ml of $CH_2Cl_2$ gave after 4 hours stirring, 920 mg of a white solid after silica gel chromatography (8:2 $CH_2Cl_2$/EtoAc).

NMR ($CDCl_3$) 1.42 (s) 9H (t-bu); 1.55 (s) 9H (t-bu); 2.31 (s) 6H (2oAC); 3.41, 3.62 (d of d, J=18 Hz) 2H ($CH_2S$); 4.73, 4.77 (d of d, J=17 Hz) 2H ($CH_2OCOAr$); 5.06 5.39 d of d, J=16 Hz) 2H ($OCH_2CO$); 5.09 (d, J=7 Hz) 1H (C6); 5.97 (d of d, J=7 Hz J=10 Hz) 1H (C7); 7.03 (s) 1H (thiazole); 7.29 (d, J=8 Hz (e.c.) 1H (Ar); 7.85 (d, J=2 Hz) 1H (Ar); 7.95 (d of d, J=2 Hz, J=8 Hz) 1H (Ar); 8.63 (d, J=10 Hz) 1H (NH). IR (KBr): 3400, 1780, 1722, 1682. UV (EtOH): λmax 236 nm ($\epsilon$=27,500). M.S.: M/Z 790 (M+H).

EXAMPLE 46

[6R-[6 alpha,7 beta(Z)]-7-[[(2-amino-4-thiazolyl)[(carboxymethoxy)imino]acetyl]amino]-3-[[3,4-dihydroxybenzoyl)oxy]methyl]-8-oxo-5-thia-1-azabicyclo[4.2.0]-oct-2-ene-2-carboxylic acid disodium salt By following the procedures and conditions described in Example 20, 920 mg (1.16 mmol) of [6R-[6 alpha,7 beta(z)]]-3-[[[3,4-bis(Acetyloxy)benzoyl]oxy]methyl]-7-[[(2-amino-4-thiazolyl)[[2-(1,1-dimethylethoxy-2-oxoethoxy]imino]acetyl]amino]-8-oxo-5-thia-1-azabicyclo[4.2.0]oct-2-ene-2-carboxylic acid 1,1-dimethylethyl ester in 24 mL of $CH_2Cl_2$ and 2.3 mL of anisole treated with 24 ml of TFA, followed by stirring the residue with EtoAc, MeOH and saturated $NaHCO_3$, gave 385 mg (62%) of a white solid after reverse phase chromatography (0–30% $CH_3CN$).

NMR ($D_2O$) 3.28, 3.56 (d of d, J=18 Hz) 2H ($CH_2S$), 4.42 (S) 2H ($CH_2CO_2Na$), 4.67, 4.96 (d of d, J=15 Hz) 2H ($CH_2O$), 5.07 (d, J=6 Hz) 1H (C6), 5.68 (d, J=6 Hz) 1H (C7), 6.71 (d, J=8 Hz) 1H (Ar) 6.87 (S) 1H (thiazole) 7.30 (m) 2H (Ar); IR (KBr): 1755, 1650, 1602; UV ($H_2O$): λmax 203 nm ($\epsilon$=17,600), λmax 231 nm ($\epsilon$=15,400), λmax 260 nm ($\epsilon$=9,800), λmax 302 ($\epsilon$=8,080);

EXAMPLE 47

(6R-trans)-7-[[(2-amino-4-thiazolyl)[[1-(aminocarbonyl)-1-methylethoxy]imino]acetyl]amino]-3-[[[3,4-bis(acetyloxy)benzoyl]oxy]methyl]-8-oxo-5-thia-1-azabicyclo[4.2.0]oct-2-ene-2-carboxylic acid 1,1-dimethylethyl ester.

A solution of 542 mg (1.01 mmol) of (6R-trans)-7-amino-3-[[[3,4-bis(acetyloxy)benzoyl]oxy]methyl]-8-oxo-5-thia-1-azabicyclo[4.2.0]oct-2-ene-2-carboxylic acid 1,1-dimethylethyl ester monohydrochloride in 25 ml $CH_2Cl_2$ was washed with 2×25 ml of saturated $NaHCO_3$/ brine (1:4). The organic solution was dried over $MgSO_4$ and filtered. To this solution was added a solution of 411 mg (1.00 mmol) of 2-2-Amino-α-[(2-amino-1,1-dimethyl-2-oxoethoxy)imino]-4-thiazole acetic acid, 136 mg (1.00 mmol) of NHBT and 211 mg (1.00 mmol) of DDC in 25 ml of dry DMF. The solution was then stirred for 24 hours giving 320 mg (42%) after silica gel chromatography.

NMR ($CDCL_3$): 1.50 (s) 6H (2 $CH_3$); 1.54 (s) 9H (t-bu); 3.42, 3.61 (d of d, J=18 Hz); 5.06 (m) 2H (½ $CH_2O$, C6); 5.32 (d, J=13 Hz) 1H (½ $CH_2O$); 5.90 (d of d, J=5 Hz, J=9 Hz) 1H (C7); 6.40 (br s) 2H ($NH_2$); 6.75 (s) 1H (thiazole); 7.28 (d, J=8 Hz) 1H (Ar); 7.83 (d, J=2 Hz) 1H (Ar); 7.93 (d of d, J=2 Hz, J=8 Hz). I.R. (KBr) 1780, 1722, 1680, 1532. UV (EtOH): λmax 236 nm ($\epsilon$=29,050). M.S.: M/Z 761 (M+H).

EXAMPLE 48

(6R-trans)-7-[[(2-amino-4-thiazolyl)[[1-(aminocarbonyl)-1-methylethoxy]imino]acetyl]amino]-3-[[(3,4-dihydroxy-benzoyl)oxy]methyl]-8-oxo-5-thia-1-azabicyclo[4.2.0]-oct-2-ene-2-carboxylic acid monosodium salt By following the procedures and conditions described in Example 20, 320 mg (0.421 mmol) of (6R-trans)-7-[[(2-amino-4-thiazolyl)[[1-(aminocarbonyl)-1-methylethoxy]imino]acetyl]amino]-3-[[[3,4-bis(acetyloxy)benzoyl]oxy]methyl]-8-oxo-5-thia-1-azabicyclo[4.2.0]-oct-2-ene-2-carboxylic acid 1,1-dimethylethyl ester in 5 mL of $CH_2Cl_2$ and 500 μL of anisole, treated with 5 mL of TFA, stirred for 3 hours and treating the residue with EtoAc, MeOH and saturated $NaHCO_3$, gave 123 mg (45%) of a white solid after reverse phase chromatography (0–30% $CH_3CN$).

NMR ($D_2O$): 1.60 (s) 6H (2 $CH_3$) 3.53, 3.78 (d of d, J=18 Hz) 2H ($CH_2S$); 4.93, 5.17 (d of d, J=13 Hz) 2H ($CH_2O$); 5.28 (d, J=4 Hz) 1H (C6); 5.90 (d, J=4 Hz) 1H (C7); 688 (d, J=8 Hz) 1H (Ar); 7.12 (s) 1H (thiazole); 7.50 (s) 1H (Ar); 7.55 (d, J=8 Hz) 1H (Ar). IR (KBr): 1762, 1672, 1605. UV ($H_2O$): λmax 218 nm ($\epsilon$=22,300). Exact mass calc. for $C_{24}H_{23}N_6O_{12}S_2N_2$: 643.0947. Found 643:0893.

What is claimed:

1. A compound of the formula

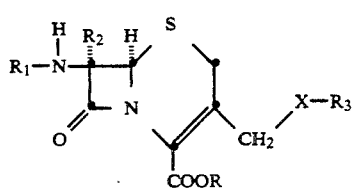

wherein X is

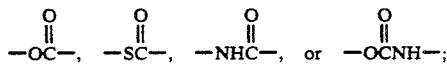

R is hydrogen or a carboxylic acid protecting group;
$R_1$ is an acyl group;
$R_2$ is hydrogen or lower alkoxy; and
$R_3$ is of the formula,

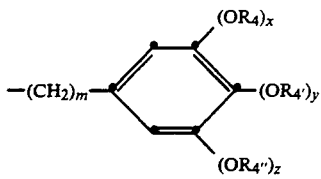

or

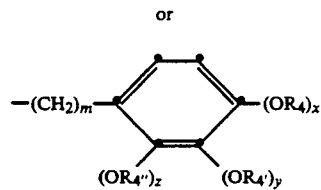

or

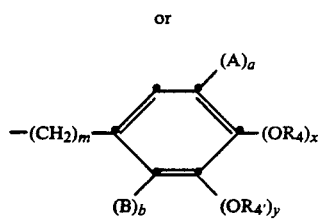

or wherein $R_4$, $R_{4'}$ and $R_{4''}$ are independently hydrogen or

wherein $R_{200}$ is straight or branched lower alkyl, A and B are halogen, a, b, x, y and z are independently zero (upon which a hydrogen atom is present at that ring position) or 1 except that at least two of x, y and z are always 1, and m is zero or an integer from 1 to 8.

2. A compound as in claim 1 wherein m is zero or 1.

3. A compound as in claim 1 wherein $R_4$, $R_{4'}$ and $R_{4''}$ are independently hydrogen or

4. A compound as in claim 1 wherein A and B are chlorine.

5. A compound as in claim 1 wherein R is hydrogen.

6. A compound as in claim 1 wherein X is

7. A compound as in claim 1 wherein X is

8. A compound as in claim 1 wherein X is

9. A compound as in claim 1 wherein X is

10. A compound as in claim 1 wherein acyl group $R_1$ is an aliphatic group of the formula

wherein $R_5$ is selected from the group consisting of alkyl, cycloalkyl, alkoxy, alkenyl, cycloalkenyl, cyclohexadienyl, or alkyl or alkenyl substituted with one or more halogen, cyano, nitro, amino, mercapto, alkylthio, or cyanomethylthio groups.

11. A compound as in claim 1 wherein acyl group $R_1$ is a carbocyclic aromatic group selected from the group consisting of

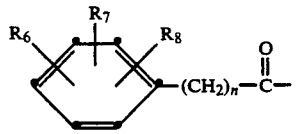

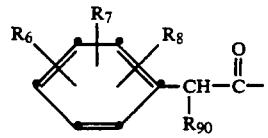

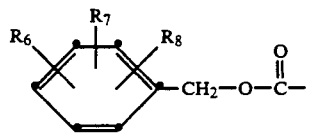

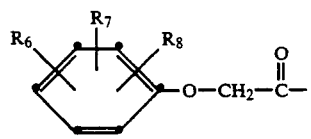

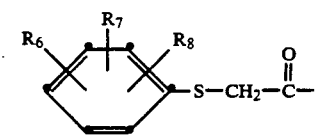

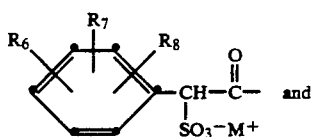 and

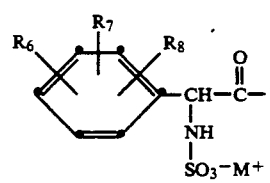

wherein n is 0, 1, 2 or 3; $R_6$, $R_7$, and $R_8$ are independently selected from the group consisting of hydrogen, halogen, hydroxyl, nitro, amino, cyano, trifluoromethyl, alkyl of 1 to 4 carbon atoms, alkoxy of 1 to 4 carbon atoms or aminomethyl; and R₉₀ is selected from the group consisting of amino, acylamino, hydroxyl, a carboxyl salt, protected carboxy, azido and a sulfo salt.

12. A compound as in claim 1 wherein acyl group R₁ is a heteroaromatic group selected from the group consisting of

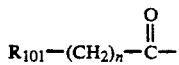

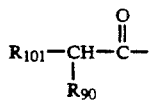

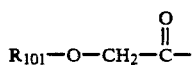

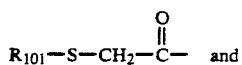

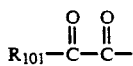

wherein n is 0, 1, 2 or 3; R₉₀ is selected from the group consisting of amino, acylamino, hydroxyl, a carboxyl salt, protected carboxy, azido and a sulfo salt; and R¹⁰¹ is a substituted or unsubstituted 5-, 6- or 7-membered heterocyclic ring containing 1, 2, 3 or 4 nitrogen, oxygen or sulfur atoms, the heterocyclic ring being substituted with halogen, hydroxy, nitro, amino, cyano, trifluoromethyl, alkyl of 1 to 4 carbon atoms, or alkoxy of 1 to 4 carbon atoms.

13. A compound as in claim 1 wherein acyl group R₁ is a substituted acetyl group of the formula

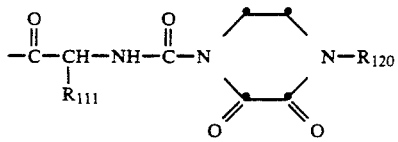

wherein R₁₁₁ is alkyl, hydroxyalkyl or an aromatic group of the formula

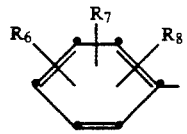

wherein R₆, R₇ and R₈ are independently selected from the group consisting of hydrogen, halogen, hydroxyl, nitro, amino, cyano, trifluoromethyl, alkyl of 1 to 4 carbon atoms, alkoxy of 1 to 4 carbon atoms, aminomethyl, or a substituted or unsubstituted 5-, 6- or 7-membered heterocyclic ring containing 1, 2, 3 or 4 nitrogen, oxygen or sulfur atoms, the heterocyclic ring being substituted with halogen, hydroxy, nitro, amino, cyano, trifluoromethyl, alkyl of 1 to 4 carbon atoms, or alkoxy of 1 to 4 carbon atoms, and R₁₂₀ is alkyl or substituted alkyl, the substituted alkyl group being substituted with one or more halogen, cyano, nitro, amino or mercapto groups.

14. A compound as in claim 1 wherein acyl group R₁ is an (acylamino) substituted acetyl group of the formula

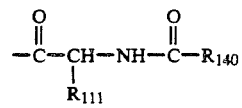

wherein R₁₁₁ is alkyl, hydroxyalkyl or an aromatic group of the formula

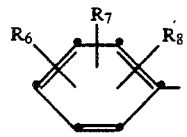

wherein R₆, R₇ and R₈ are independently selected from the group consisting of hydrogen, halogen, hydroxyl, nitro, amino, cyano, trifluoromethyl, alkyl of 1 to 4 carbon atoms, alkoxy of 1 to 4 carbon atoms, aminomethyl, or a substituted or unsubstituted 5-, 6- or 7-membered heterocyclic ring containing 1, 2, 3 or 4 nitrogen, oxygen or sulfur atoms, the heterocyclic ring being substituted with halogen, hydroxy, nitro, amino, cyano, trifluoromethyl, alkyl of 1 to 4 carbon atoms, or alkoxy of 1 to 4 carbon atoms, and R₁₄₀ is

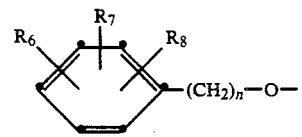

(where R₆, R₇ and R₈ are as previously defined and n is 0, 1, 2 or 3), hydrogen, lower alkyl, lower alkyl substituted with halo, trifluoromethyl, amino and cyano, amino alkylamino, dialkylamino, (cyanoalkyl)amino, hydrazino, alkyl hydrazino, aryl hydrazino and acyl hydrazino.

15. A compound as in claim 1 wherein acyl group R₁ is a (substituted acylimino) substituted acetyl group having the formula

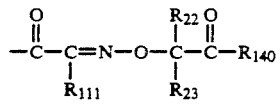

wherein R₁₁₁ is alkyl, hydroxyalkyl or an aromatic group of the formula

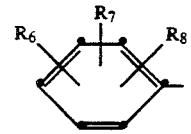

wherein R₆, R₇ and R₈ are independently selected from the group consisting of hydrogen, halogen, hydroxyl, nitro, amino, cyano, trifluoromethyl, alkyl of 1 to 4 carbon atoms, alkoxy of 1 to 4 carbon atoms, aminomethyl, or a substituted or unsubstituted 5-, 6- or 7-membered heterocyclic ring containing 1, 2, 3 or 4 nitrogen, oxygen or sulfur atoms, the heterocyclic ring being substituted with halogen, hydroxy, nitro, amino, cyano, trifluoromethyl, alkyl of 1 to 4 carbon atoms, or alkoxy of 1 to 4 carbon atoms, and R$_{140}$ is

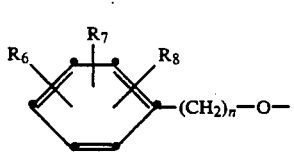

(wherein R$_6$, R$_7$ and R$_8$ are as defined above and n is 0, 1, 2 or 3), hydrogen, lower alkyl, lower alkyl substituted with halo, trifluoromethyl, amino and cyano, amino, alkylamino, dialkylamino, (cyanoalkyl) amino, hydrazino, alkyl hydrazino, aryl hydrazino and acyl hydrazino, and R$_{22}$ and R$_{23}$ are independently selected from the group consisting of hydrogen and lower alkyl, or R$_{22}$ and R$_{23}$ taken together with the carbon atom to which they are attached form a C$_3$-C$_7$ carbocyclic ring.

16. A compound as in claim 1 wherein acyl group R$_1$ is a substituted acetyl group of the formula

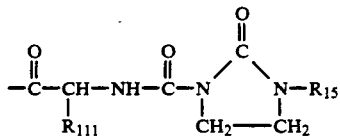

wherein R$_{111}$ is alkyl, hydroxyalkyl or an aromatic group of the formula

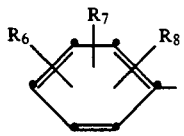

wherein R$_6$, R$_7$ and R$_8$ are independently selected from the group consisting of hydrogen, halogen, hydroxyl, nitro, amino, cyano, trifluoromethyl, alkyl of 1 to 4 carbon atoms, alkoxy of 1 to 4 carbon atoms, aminomethyl, or a substituted or unsubstituted 5-, 6- or 7-membered heterocyclic ring containing 1, 2, 3 or 4 nitrogen, oxygen or sulfur atoms, the heterocyclic ring being substituted with halogen, hydroxy, nitro, amino, cyano, trifluoromethyl, alkyl of 1 to 4 carbon atoms, or alkoxy of 1 to 4 carbon atoms, and R$_{15}$ is hydrogen, alkylsulfonyl, arylmethyleneamino (i.e., —N=CHR$_{11}$ wherein R$_{111}$ is as defined above),

(wherein R$_{16}$ is hydrogen, alkyl or halogen substituted alkyl), aromatic group (as defined by R$_{111}$ above), alkyl or substituted alkyl, the substituted alkyl group being substituted with one or more halogen, cyano, nitro, amino or mercapto groups.

17. A compound as in claim 1 wherein acyl group R$_1$ is of the formula

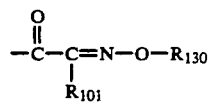

wherein R$_{101}$ is an unsubstituted or substituted 5, 6- or 7-membered heterocyclic ring containing 1, 2, 3 or 4 nitrogen, oxygen or sulfur atoms wherein the heterocyclic ring is substituted by halogen, hydroxy, nitro, amino, cyano, trifluoromethyl, C$_1$ to C$_4$ alkyl or C$_1$ to C$_4$ alkoxy and R$_{130}$ is hydrogen, lower alkyl, C$_3$-C$_7$ cycloalkyl and substituted lower alkyl wherein the lower alkyl is substituted with one or more halogen, cyano, nitro, amino, mercapto, lower alkylthio, carboxyl (including salts thereof), amido, lower alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, diloweralkoxyphosphinyl carboxyl lower alkyl or carboxyl-3,7-cycloalkyl.

18. A compound as in claim 17 wherein acyl group R$_{101}$ is of the formula

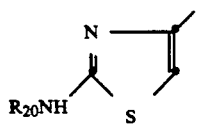

wherein R$_{20}$ is hydrogen or an amino protecting group, and R$_{130}$ is hydrogen, lower alkyl or a group of the formula

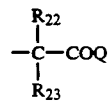

wherein R$_{22}$ and R$_{23}$ are selected from the group consisting of hydrogen and lower alkyl or taken together with the carbon atom to which they are attached form a C$_3$-C$_7$ carbocyclic ring, and Q is hydroxy or NHR$_{19}$ where R$_{19}$ is hydrogen or lower alkyl, amino, alkyl amino, aryl amino or acyl amino.

19. A compound as in claim 18 wherein R$_{20}$ is hydrogen or triphenylmethyl.

20. A compound as in claim 1, which is [6R-[6 alpha,7 beta(Z)]]-7-[[[(2-amino-4-thiazolyl)(methoxyimino)acetyl]amino]-3-[[[(3,4-dihydroxyphenyl)carbonyl]oxy]methyl]-8-oxo-5-thia-1-azabicyclo[4.2.0]-oct-2-ene-2-carboxylic acid monosodium salt.

21. A compound as in claim 1, which is [6R-[6 alpha,7 beta(Z)]]-3-[[[3,4-bis(acetyloxy)benzoyl]oxy]methyl]-7-[[[2-amino-4-thiazolyl][(2-amino-2-oxoethoxy)imino]acetyl]amino]-8-oxo-5-thia-1-azabicyclo[4.2.-0]oct-2-ene-2-carboxylic acid monosodium salt.

22. A compound as in claim 1, which is [6R-[6 alpha,7 beta(Z)]]-7-[[[(2-amino-4-thiazolyl)[1-carboxyl-1-methyl ethoxy]imino]acetyl]amino]-3-[[(3,4-dihydroxybenzoyl)oxy]methyl]-8-oxo-5-thia-1-azabicyclo[4.2.0]-oct-2-ene-2-carboxylic acid disodium salt.

23. A compound as in claim 1, which is [6R-[6 alpha,7 beta(R*)]]-7-[[[[(4-ethyl-2,3-dioxo-1-piperazinyl)carbonyl]amino]phenylacetyl]amino]-3-[[[(3,4-dihydroxy)benzoyl]oxy]methyl]-8-oxo-5-thia-1-azabicyclo[4.2.-0]oct-2-ene-carboxylic acid monosodium salt.

24. A compound as in claim 1, which is [6R-[6 alpha,7 beta(Z)]]-7-[[(2-amino-4-thiazolyl)(methoxyimino)acetyl]amino]-3-[[[(3,4-bis(acetyloxy)benzoyl)]oxy]methyl]-8-oxo-5-thia-1-azabicyclo[4.2.0]oct-2-ene-2-carboxylic acid monosodium salt.

25. A compound as in claim 1, which is [6R-[6 alpha,7 beta(Z)]]-7-[[(2-amino-4-thiazolyl)(methoxyimino)acetyl]amino]-3-[[[(2,3-dihydroxyphenyl)carbonyl]oxy]methyl]-8-oxo-thia-1-azabicyclo[4.2.0]oct-2-ene-2-carboxylic acid monosodium salt.

26. A compound as in claim 1, which is [6R-trans)-3-[[[3,4-bis(acetyloxy)benzoyl]oxy]methyl]-8-oxo-7-[(phenoxyacetyl)amino]-5-thia-1-azabicyclo[4.2.0]oct-2-ene-2-carboxylic acid monosodium salt.

27. A compound as in claim 1, which is (6R-trans)-7-amino-3-[[[3,4-bis(acetyloxy)benzoyl]oxy]methyl]-8-oxo-5-thia-1-azabicyclo[4.2.0]oct-2-ene-2-carboxylic acid 1,1-dimethylethyl ester monohydrochloride.

28. A compound as in claim 1, which is [6R-[6 alpha,7 beta(Z)]]-3-[[[3,4,5-tris(acetyloxy)benzoyl]oxy]methyl]-7-[[(2-amino-4-thiazolyl)(methoxyimino)acetyl]amino]-8-oxo-5-thia-1-azabicyclo[4.2.0]oct-2-ene-2-carboxylic acid monosodium salt.

29. A compound as in claim 1, which is [6R-[6 alpha,7 beta(Z)]]-7-[[(2-amino-4-thiazolyl)(methoxyimino)acetyl]amino]-3-[[2-(3,4-dihydroxyphenyl)-1-oxoethyl]methyl]-8-oxo-5-thia-1-azabicyclo[4.2.0]oct-2-ene-2-carboxylic acid monosodium salt.

30. A compound as in claim 1, which is [6R-[6 alpha,7 beta(Z)]]-3-[[[3,4-bis(acetyloxy)benzoyl]oxy]methyl]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid disodium salt.

31. A compound as in claim 1, which is (6R-trans)-7-amino-3-[[[3,4-bis(acetyloxy)benzoyl]thio]methyl]-8-oxo-5-thia-1-azabicyclo[4.2.0]oct-2-ene-2-carboxylic acid 1,1-dimethylethyl ester monohydrochloride.

32. A compound as in claim 1, which is [6R-[6 alpha,7 beta(S)*)]]-3-[[[3,4-bis(acetyloxy)benzoyl]oxy]methyl]-7-[[[[(4-ethyl-2,3-dioxo-1-piperazinyl)carbonyl]amino]phenylacetyl]amino]-8-oxo-5-thia-1-azabicyclo[4.2.0]oct-2-ene-2-carboxylic acid monosodium salt.

33. A compound as in claim 1, which is [6R-cis)-3-[[[3,4-bis(acetyloxy)benzoyl]oxy]methyl]-7-methoxy-8-oxo-7-[(2-thienylacetyl)amino]-5-thia-1-azabicyclo[4.2.0]oct-2-ene-2-carboxylic acid monosodium salt.

34. A compound as in claim 1, which is [6R-cis)-3-[[(3,4-dihydroxybenzoyl)oxy]methyl]-7-methoxy-8-oxo-7-[(2-thienylacetyl)amino]-5-thia-1-azabicyclo[4.2.0]oct-2-ene-2-carboxylic acid monosodium salt.

35. A compound as in claim 1, which is [6R-[6 alpha,7 beta(Z)]]-7-[[(2-amino-4-thiazolyl)(methoxyimino)acetyl]amino]-3-[[[(3,4bis(acetyloxy)-2,5-dichlorobenzoyl)]oxy]methyl]-8-oxo-5-thia-1-azabicyclo[4.2.0]oct-2-ene-2-carboxylic acid monosodium salt.

36. A compound as in claim 1, which is [6R-[6 alpha,7 beta(Z)]]-3-[[[[3,4-bis(acetyloxy)phenyl]amino]carbonyl]oxy]methyl]-7-[[(2-amino-4-thiazolyl)(methoxyimino)acetyl]amino]-8-oxo-5-thia-1-azabicyclo[4.2.0]oct-2-ene-2-carboxylic acid monosodium salt.

37. A compound as in claim 1, which is [6R-[6 alpha,7 beta(Z)]]-3-[[[[3,4-bis(acetyloxy)phenyl]amino]carbonyl]oxy]methyl]-7[[[[2-amino-[2-amino-2-oxoethoxy]imino]-4-thiazolyl]acetyl]amino]-8-oxo-5-thia-1-azabicyclo[4.2.0]oct-2-ene-2-carboxylic acid monosodium salt.

38. A compound as in claim 1, which is [6R-[6 alpha,7 beta(Z)]]-7-[[(2-amino-4-thiazolyl)(methoxyimino)acetyl]amino]-3-[[[(3,4-dihydroxybenzoyl)thio]methyl]-8-oxo-5-thia-1-azabicyclo[4.2.0]oct-2-ene-2-carboxylic acid monosodium salt.

39. A compound as in claim 1, which is [6R-[6 alpha,7 beta(Z)]]-7-[[(2-amino-4-thiazolyl)(methoxyimino)acetyl]amino]-3-[[[(3,4-bis(acetyloxy)benzoyl)]thio]methyl]-8-oxo-5-thia-1-azabicyclo[4.2.0]oct-2-ene-2-carboxylic acid monosodium salt.

40. A compound as in claim 1, which is [6R-[6 alpha,7 beta(Z)]]-3-[[[(3,4-bis(acetyloxy)benzoyl]amino]methyl]-7-[[(2-amino-4-thiazolyl)(methoxyimino)acetyl]amino]-5-thia-1-azabicyclo[4.2.0]oct-2-ene-2-carboxylic acid monosodium salt.

41. A compound as in claim 1, which is [6R-[6 alpha,7 beta(Z)]]-3-[[[(3,4-dihydroxy)benzoyl]amino]methyl]-7-[[(2-amino-4-thiazolyl)(methoxyimino)acetyl]amino]-5-thia-1-azabicyclo[4.2.0]oct-2-ene-2-carboxylic acid monosodium salt.

42. A compound as in claim 1, which is [6R-[6 alpha,7 beta(Z)[[-7-[[[2-amino-[(2-amino-2-oxoethoxy)imino]-4-thiazolyl]acetyl]amino]-3-[[(3,4-dihydroxybenzoyl)oxy]methyl]-8-oxo-5-thia-1-azabicyclo-[4.2.0]oct-2-ene-2-carboxylic acid monosodium salt.

43. A compound as in claim 1, which is [6R-[6 alpha,7 beta(Z)[[-7-[[[2-amino[(2-amino-2-oxoethoxy)imino]-4-thiazolyl]acetyl]amino]-3-[[(3,4-dihydroxybenzoyl)thio]-methyl]-8-oxo-5-thia-1-azabicyclo-[4.2.0]oct-2-ene-2-carboxylic acid monosodium salt.

44. A compound as in claim 1, which is [6R-[6 alpha,7 beta(Z)[[-7-[[2-amino-4-thiazolyl)[(carboxymethoxy)imino]acetyl]amino]-3-[[3,4-dihydroxybenzoyl)oxy]methyl]-8-oxo-5-thia-1-azabicyclo[4.2.0]-oct-2-ene-2-carboxylic acid disodium salt.

45. A compound as in claim 1, which is (6R-trans)-7-[[(2-amino-4-thiazolyl)[1-(aminocarbonyl)-1-methylethoxy]imino]-acetyl]amino]-3-[[(3,4-dihydroxy-benzoyl)oxy]methyl]-8-oxo-5-thia-1-azabicyclo[4.2.0]-oct-2-ene-2-carboxylic acid monosodium salt.

* * * * *

UNITED STATES PATENT AND TRADEMARK OFFICE
CERTIFICATE OF CORRECTION

PATENT NO. : 5,189,157
DATED : February 23, 1993
INVENTOR(S) : Chung-Chen Wei and Kevin F. West It is certified that error appears in the above-identified patent and that said Letters Patent is hereby corrected as shown below:

On the title page, delete item:

" [75] Inventors: Ching-Chen Wei, Cedar Knolls;
        Kevin F. West, Fairfield, both of NJ"

and insert therefor

-- [75] Inventors: Chung-Chen Wei, Cedar Knolls;
        Kevin F. West, Fairfield, both of NJ --.

In claim 13, column 41, line 37, insert the following between "a" and "substituted":  -- [[[4-substituted-2,3-dioxo-1-piperzinyl]carbonyl]amino] --

In claim 16, column 43, line 24, insert the following between "a" and "substituted":  -- [[[3-substituted-2-oxo-1-imidazolidinyl]carbonyl]amino] --;

In claim 16, column 43, line 54, change "(i.e., $-N=CHR_{11}$" to -- (i.e., $-N=CHR_{111}$ --.

Signed and Sealed this

Thirtieth Day of November, 1993

Attest:

BRUCE LEHMAN

Attesting Officer

Commissioner of Patents and Trademarks